US012523644B2

(12) United States Patent
Kinney et al.

(10) Patent No.: US 12,523,644 B2
(45) Date of Patent: Jan. 13, 2026

(54) METHODS AND SYSTEMS FOR NUCLEIC ACID SEQUENCING USING NANOPORES

(71) Applicant: Western Digital Technologies, Inc., San Jose, CA (US)

(72) Inventors: Justin P. Kinney, San Jose, CA (US); Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 219 days.

(21) Appl. No.: 18/499,069

(22) Filed: Oct. 31, 2023

(65) Prior Publication Data

US 2025/0137991 A1 May 1, 2025

(51) Int. Cl.
*G01N 33/487* (2006.01)

(52) U.S. Cl.
CPC .............................. *G01N 33/48721* (2013.01)

(58) Field of Classification Search
None
See application file for complete search history.

(56) References Cited

U.S. PATENT DOCUMENTS

| | | | | |
|---|---|---|---|---|
| 9,017,937 | B1 * | 4/2015 | Turner | C12Q 1/6869 435/6.1 |
| 10,883,140 | B2 | 1/2021 | Church et al. | |
| 2011/0224098 | A1 | 9/2011 | Luan et al. | |
| 2013/0240359 | A1 | 9/2013 | Turner et al. | |
| 2014/0051068 | A1 | 2/2014 | Cherf et al. | |
| 2016/0153105 | A1 | 6/2016 | Gumbercht | |
| 2019/0309008 | A1 | 10/2019 | Ju et al. | |
| 2020/0038868 | A1 | 2/2020 | So et al. | |
| 2020/0318180 | A1 | 10/2020 | Gunderson et al. | |
| 2021/0268503 | A1 * | 9/2021 | Soper | G11C 11/1655 |
| 2022/0299472 | A1 | 9/2022 | Maney, Jr. et al. | |
| 2023/0176032 | A1 | 6/2023 | Bedau et al. | |
| 2023/0176033 | A1 | 6/2023 | Bedau et al. | |

OTHER PUBLICATIONS

International Search Report and Written Opinion from PCT App. No. PCT/US2024/035679 (filed Jun. 26, 2024), mailed Oct. 18, 2024.

(Continued)

*Primary Examiner* — J. Christopher Ball

(57) ABSTRACT

A method of performing nucleic acid sequencing may comprise using a disintegrator situated in a fluidic channel of a sequencing device to cleave off a portion of a nucleic acid molecule in the fluidic channel; applying an electrostatic force to divert the portion of the nucleic acid molecule through a nanopore; detecting an ionic current through the nanopore; and determining an identity of at least one nucleotide of the portion of the nucleic acid molecule based at least in part on the ionic current. A system for sequencing nucleic acids may comprise an array comprising a plurality of sequencing devices, each comprising a fluidic channel, a disintegrator embedded in the fluidic channel, and a nanopore coupled to an exit end of the fluidic channel; and detection circuitry coupled to the array and configured to detect ionic currents through the nanopores.

25 Claims, 16 Drawing Sheets

(56) References Cited

OTHER PUBLICATIONS

Breyer, W.A. and Matthews, B.W., Structure of *Escherichia coli* exonuclease I, Nature structural biology, 7(12), pp. 1125-1128, 2000.

Kumarevel, T., Mizuno, H. and Kumar, P.K., Characterization of the metal ion binding site in the anti-terminator protein, HutP, of Bacillus subtilis. Nucleic acids research, 33(17), pp. 5494-5502, 2005.

Lau, M.W., Trachman, R.J. and Ferré-D'Amaré, A.R., A divalent cation dependent variant of the glmS ribozyme with stringent Ca2+ selectivity cooptsa preexisting nonspecific metal ion-binding site. Rna, 23(3), pp. 355-364, 2017.

Lovett, S.T., The DNA exonucleases of *Escherichia coli*. EcoSal Plus, 4(2), 2011.

Lu, D. and Keck, J.L., Structural basis of *Escherichia coli* single-stranded DNA binding protein stimulation of exonuclease I, Proceedings of the National Academy of Sciences, 105(27), pp. 9169-9174, 2008.

Mcbride, M.B., Reactions controlling heavy metal solubility in soils. Advances in Soil Science: vol. 10, pp. 1-56, 1989.

Wang, C. et al., "Clog-free translocation of long DNA in nanofluidic pillar arrays and 30 nm wide channels: A fabrication and hydrodynamic study." in 18th International Conference on Miniaturized Systems for Chemistry and Life Sciences, MicroTAS 2014 (pp. 1347-1349).

Werner, J.H., Cai, H., Keller, R.A. and Goodwin, P.M., Exonuclease I hydrolyzes DNA with a distribution of rates. Biophysical journal, 88(2), pp. 1403-1412, 2005.

Yusuke Goto et al., "Silicon nitride nanopore created by dielectric breakdown with a divalent cation: deceleration of translocation speed and identification of single nucleotides," Nanoscale, Issue 30, 2019.

Yusuke Goto et al., Electronic Supplementary Information for "Silicon nitride nanopore created by dielectric breakdown with a divalent cation:deceleration of translocation speed and identification of single nucleotides," Electronic Supplementary Material (ESI) for Nanoscale, The Royal Society of Chemistry, 2019.

International Search Report and Written Opinion from PCT Application No. PCT/US2024/039072 (filed Jul. 23, 2024), mailed Nov. 4, 2024.

Office Action dated Aug. 18, 2025 from U.S. Appl. No. 18/499,024 (filed Oct. 31, 2025).

* cited by examiner

METHODS AND SYSTEMS FOR NUCLEIC ACID SEQUENCING USING NANOPORES

BACKGROUND

Nucleic acids are negatively-charged polyelectrolytes with four monomers that are covalently bonded to form polymer chains. For deoxyribonucleic acid (DNA), the monomers are the nucleotides adenine (A), thymine (T), guanine (G), and cytosine (C). For ribonucleic acid (RNA), they are A, C, G, and uracil (U).

The use of biomolecules, including DNA, RNA, and proteins, to store data has been proposed due to the density, stability, energy-efficiency, and longevity of biomolecules. For example, a human cell has a mass of about 3 picograms and stores around 6.4 GB of information. The volumetric density of DNA is estimated to be 1,000 times greater than that of flash memory, and its energy consumption 108 times less than that of flash memory. In addition, the retention time of DNA is significantly greater than that of electronic memory. Thus, DNA can store information reliably over time.

Information bits can be encoded into biomolecules, such as nucleic acid strands, using a variety of techniques. Once encoded, the biomolecules can later be read using a structure called a nanopore, which is a small hole, typically 1-2 nm in diameter and a couple of nanometers thick. There are two types of nanopore: biological (also referred to as protein) nanopores and solid-state nanopores. A biological nanopore is made from a pore material embedded in a lipid membrane. A solid-state nanopore is a nanoscale (e.g., nanometer-sized) opening in a synthetic membrane (e.g., SiNx, $SiO_2$, etc.).

In conventional systems, a target biomolecule, such as a nucleic acid strand, in an electrolyte solution can be driven through a nanopore (biological or solid-state), primarily by electrophoresis, and read. A highly-focused external electric field applied transverse to and in the vicinity of the nanopore (e.g., by sensing electrodes used to read or detect the biomolecule) acts on a relatively short segment of the negatively charged biomolecule and directs it through the hole in the nanopore. FIG. 1 illustrates a nanopore 15 with a biomolecule 20 (e.g., a single-stranded DNA (ssDNA) molecule), passing through it. Two sensing electrodes 18 are situated near the nanopore 15 to sense the ionic current through the nanopore 15. The sensing electrodes 18 are typically connected to a voltage source 30, which supplies a voltage to the sensing electrodes 18.

As the molecule 20 passes through the nanopore 15, the ions occupying the pore are excluded, which causes changes in the ionic current and/or electronic signal measured across the nanopore 15 (e.g., using the sensing electrodes 18 on opposite sides of the nanopore), which can be observed and used to detect constituent parts of the molecule 20 (e.g., nucleotides of a DNA strand). For example, as nucleic acid moves, or translocates in the translocation direction 16, through the nanopore 15, different nucleotides cause different ionic current patterns. Specifically, the nucleotides cause distinct, measurable ionic current blockades, or current drops, as they pass through the nanopore 15. The current blockades can be recorded (e.g., using a current amplifier) and converted into digital signals (e.g., using an analog-to-digital converter). These current blockades, or patterns of them, can be used to distinguish between different nucleotides. For example, by analyzing the amplitudes, durations, frequencies, and shapes of the blockade events, various properties of the target molecule 20 can be obtained.

The duration of each current blockade is dependent on the translocation or dwell time of the molecule 20 passing through the nanopore 15. One challenge with using solid-state nanopores is that the thickness of the synthetic membrane is typically much larger than the size of a single nucleotide. As a result, as the molecule 20 passes through the nanopore 15, multiple nucleotides are inside of the nanopore 15 and are together causing changes in the ionic current. Consequently, the measured current is captures a convolution of the contributions of individual nucleotides. To determine the identities of the individual nucleotides, the measured current must be processed, which can be computationally expensive and prone to errors.

The conventional solution to this problem is to try to minimize the thickness of the synthetic membrane so that only one nucleotide is within the nanopore 15 at a time. Manufacturing such thin membranes is difficult, however. Moreover, controlling the size (e.g., diameter, uniformity, etc.) of nanopores in very thin membranes is challenging. An additional problem is durability because a membrane having such a small thickness typically degrades rapidly in an aqueous environment.

Therefore, there is a need for improvements.

SUMMARY

This summary represents non-limiting embodiments of the disclosure.

Disclosed herein are devices, systems, and methods for sequencing nucleic acids using a nanopore. In some embodiments, a nucleic acid molecule is fragmented into smaller portions (e.g., as small as individual nucleotides), which are then routed, in order, through a nanopore for detection. This approach results in high resolution sequencing (e.g., at the individual nucleotide level) that is independent of the thickness of the membrane. The disclosed techniques decouple signal quality from the translocation speed of nucleotides. In some embodiments, the membrane can be made thicker and multiple current samples taken for each nucleotide. As a result, for any translocation speed within a range, the thickness of the membrane can be tuned (e.g., increased up to some limit) to allow multiple ionic current samples per nucleotide, which provides a boost in signal-to-noise ratio (SNR). As a result, manufacturability and resolution can both be improved relative to conventional approaches.

A sequencing device can include a disintegrator that removes portions of a nucleic acid molecule (e.g., individual nucleotides), in sequence, from a strand of nucleotides (e.g., ssDNA), and a nanopore that measures current blockades caused by the portions of the nucleic acid molecule, in order. The relative rates of disintegration and translocation through the nanopore can be tuned and/or controlled to ensure that the nucleotides are sequenced in order. A pair of electrodes can be included to direct the portions of the nucleic acid molecule through the nanopore.

A system may include an array of disintegrators and nanopores in one-to-one relationships to sequence (fragments of) a target molecule. A processor may be included to perform an assembly procedure using measured currents and/or identified nucleotides from the sequenced fragments.

In some aspects, the techniques described herein relate to a method of performing nucleic acid sequencing, the method including: using a disintegrator situated in a fluidic channel of a sequencing device, cleaving off a portion of a nucleic acid molecule in the fluidic channel; applying an electrostatic force to divert the portion of the nucleic acid molecule through a nanopore; detecting an ionic current through the nanopore; and determining an identity of at least one nucleotide of the portion of the nucleic acid molecule based at least in part on the ionic current.

In some aspects, the portion of the nucleic acid molecule is a single nucleotide, and the identity of the at least one nucleotide of the portion of the nucleic acid molecule is an identity of the single nucleotide.

In some aspects, the portion of the nucleic acid molecule is an amino acid, and wherein cleaving off the portion of the nucleic acid molecule includes breaking a glycosidic bond to cleave off the amino acid.

In some aspects, the portion of the nucleic acid molecule is a nucleoside, and wherein cleaving off the portion of the nucleic acid molecule includes breaking a phosphoester bond to cleave off the nucleoside.

In some aspects, the portion of the nucleic acid molecule is an oligonucleotide.

In some aspects, cleaving off the portion of the nucleic acid molecule includes a catalytic moiety cleaving off the portion of the nucleic acid molecule.

In some aspects, the catalytic moiety includes a divalent cation.

In some aspects, cleaving off the portion of the nucleic acid molecule includes applying chemical hydrolysis.

In some aspects, applying chemical hydrolysis includes using a reactive oxygen species (ROS).

In some aspects, cleaving off the portion of the nucleic acid molecule includes inducing electrolysis.

In some aspects, cleaving off the portion of the nucleic acid molecule includes exposing a contents of the fluidic channel to UVA radiation.

In some aspects, the method further includes straightening the nucleic acid molecule before cleaving off the portion of the nucleic acid molecule.

In some aspects, straightening the nucleic acid molecule includes directing the nucleic acid molecule through a structure situated in the fluidic channel.

In some aspects, the structure includes at least one of: (a) a progressive geometry structure, (b) a quasi-two-dimensional structure, or (c) a three-dimensional structure.

In some aspects, the method further includes an assistive element enhancing operation of the disintegrator.

In some aspects, detecting the ionic current through the nanopore includes sampling the ionic current a plurality of times while the portion of the nucleic acid molecule traverses the nanopore.

In some aspects, the method further includes controlling a speed of the nucleic acid molecule through the disintegrator.

In some aspects, controlling the speed of the nucleic acid molecule through the disintegrator includes applying a voltage through an electrode pair to control the speed of the nucleic acid molecule through the disintegrator.

In some aspects, controlling the speed of the nucleic acid molecule through the disintegrator includes applying hydrostatic pressure to control a speed of the nucleic acid molecule through the disintegrator.

In some aspects, the techniques described herein relate to a system for sequencing nucleic acids, the system including: an array including a plurality of sequencing devices, each of the plurality of sequencing devices in the array including a respective fluidic channel, a respective disintegrator embedded in the respective fluidic channel, and a respective nanopore coupled to an exit end of the respective fluidic channel; and detection circuitry coupled to the array and configured to detect a plurality of nanopore currents, each of the plurality of nanopore currents corresponding to a respective sequencing device in the array.

In some aspects, each of the plurality of sequencing devices in the array further includes a respective straightener.

In some aspects, the respective straightener includes at least one of: (a) a progressive geometry, (b) a quasi-two-dimensional structure, (c) a three-dimensional structure, (d) a plurality of pillars, (e) a funnel, or (f) a plurality of spheres.

In some aspects, each respective fluidic channel includes a respective horizontal portion and a respective vertical portion.

In some aspects, each respective nanopore is situated at an exit end of the respective vertical portion of the respective fluidic channel.

In some aspects, a thickness of each respective nanopore is larger than a pitch of a single nucleotide.

In some aspects, each respective disintegrator includes a catalytic moiety embedded in the respective fluidic channel.

In some aspects, the catalytic moiety includes a divalent cation.

In some aspects, each respective disintegrator is configured to apply chemical hydrolysis.

In some aspects, the array further includes a wire, and further including a power source coupled to the wire and configured to induce electrolysis.

In some aspects, each respective disintegrator includes a respective waveguide configured to generate evanescent waves to expose a contents of the respective fluidic channel to UVA radiation.

In some aspects, the system further includes a processor configured to perform an assembly process using at least two of the plurality of nanopore currents.

BRIEF DESCRIPTION OF THE DRAWINGS

Objects, features, and advantages of the disclosure will be readily apparent from the following description of certain embodiments taken in conjunction with the accompanying drawings in which.

Figure 1:
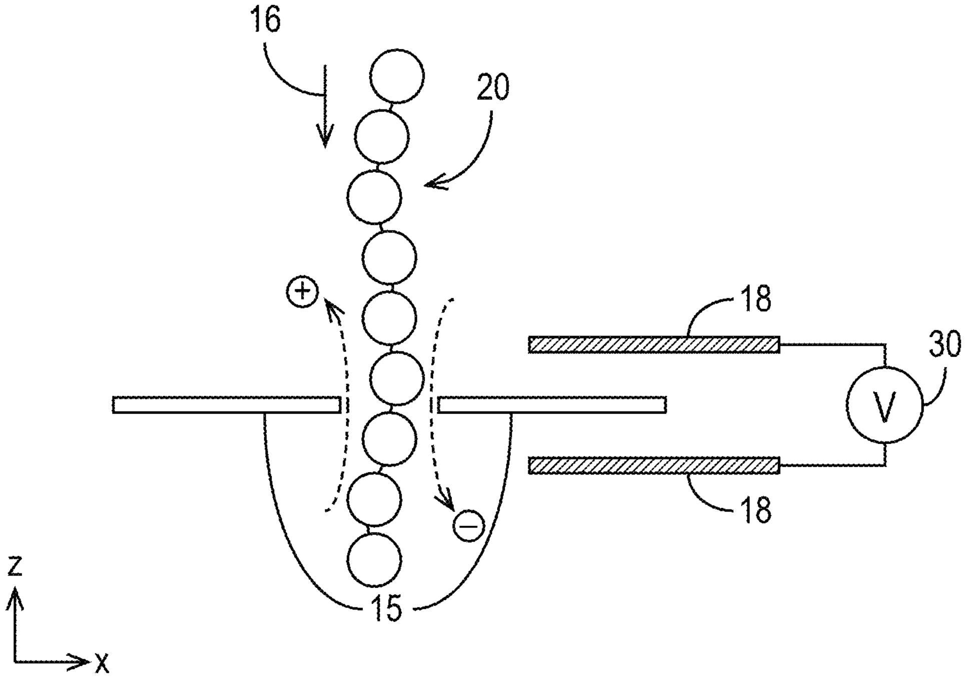
FIG. 1 illustrates a nanopore with a biomolecule passing through it.

To facilitate understanding, identical reference numerals have been used, where possible, to designate identical elements that are common to the figures. It is contemplated that elements disclosed in one embodiment may be beneficially utilized in other embodiments without specific recitation. Moreover, the description of an element in the context of one drawing is applicable to other drawings illustrating that element.

Many of the drawings herein illustrate multiple instances of a particular element (e.g., sequencing devices 401, pillars 111, etc.). Individual instances of elements are labeled by a reference number followed by a letter. For convenience, the written description sometimes refers generally to these items using only the reference number.

It is to be appreciated that unless context indicates otherwise, letters following reference numerals are intended to distinguish between like elements within individual drawings. The appearance of a particular reference numeral and letter in different drawings does not necessarily mean the identified elements are identical. For example, the pillar 111A in FIG. 4B has a different shape in the illustrated plane than the pillar 111A in FIG. 4C.

DETAILED DESCRIPTION

Disclosed herein are devices, apparatuses, systems, and methods for sequencing nucleic acids using a nanopore. A disintegrator is configured to cleave off a portion of a nucleic acid, which is diverted through a nanopore for detection/sequencing. Although much of the discussion below describes fragmenting a nucleic acid molecule into individual nucleotides, it is to be appreciated that cleavage of other portions of a nucleic acid molecule are also possible using the techniques described herein. For example, the disintegrator described herein can split a nucleic acid into small oligonucleotides, which could have different sizes (e.g., due to some bonds being easier to break than others). As another example, the disintegrator can cleave off amino acids by breaking glycosidic bonds. As another example, the disintegrator can cleave off nucleosides by breaking phosphoester bonds. These and other examples are not intended to be limiting.

In some embodiments, a nucleic acid molecule is fragmented into smaller portions (e.g., individual nucleotides, amino acids, nucleosides, oligonucleotides), which are then routed individually, in order, through a nanopore for detection. This approach results in high-resolution sequencing (e.g., in some embodiments, as fine as at the individual nucleotide level) and allows the use of thicker membranes than in conventional systems. The disclosed techniques also decouple signal quality from the translocation speed of nucleotides (or portions of the nucleic acid). As a result, for any translocation speed within a range, the thickness of the membrane can be tuned (e.g., increased up to some limit) to allow multiple ionic current samples per nucleotide, which provides a boost in signal-to-noise ratio (SNR). In some embodiments, the thickness of the nanopore is larger than the pitch of a single nucleotide. As a result, manufacturability and resolution can both be improved relative to conventional approaches.

In some embodiments, a sequencing device includes a disintegrator that is formed by embedding a catalytic moiety with exonuclease-like activity (e.g., a divalent cation such as, for example, $Mg^{2+}$, $Ca^{2+}$, $Pt^{2+}$) along a portion of a fluidic channel through which the nucleic acid travels. As will be appreciated by those having ordinary skill in the art, a catalytic moiety with exonuclease-like activity refers to a functional component or group within a molecule (e.g., an enzyme (natural or synthetic), a catalytic RNA, an artificial catalytic moiety, etc.) that exhibits a biochemical activity similar to that of an exonuclease (i.e., an enzyme that can cleave nucleotides from the end of a nucleic acid molecule (DNA or RNA) in a step-by-step manner by removing one nucleotide at a time from the end of the chain). In some embodiments, the disintegrator (e.g., using a catalytic moiety) fragments the nucleic acid polymer into individual nucleotides that traverse the remainder of the fluidic channel and the nanopore individually, which provides higher signal resolution than conventional approaches. In some embodiments, the disintegrator fragments the nucleic acid polymer into smaller portions that traverse the remainder of the fluidic channel and the nanopore one by one, which also provides higher signal resolution than conventional approaches.

In some embodiments, the sequencing device also includes a straightener that is situated before the disintegrator to straighten a molecule prior to it being handled by the disintegrator. The straightener can be provided to reduce the occurrence of and/or remove secondary structures in the nucleic acid polymer, such as hairpin loops, stem-loop structures, G-quadruplex structures, pseudoknots, and other base-pairing interactions between complementary nucleotide sequences within a nucleic acid strand. If provided, the straightener can have a quasi-two-dimensional (quasi-2D) structure or a three-dimensional (3D) structure. In some embodiments, a device having a quasi-2D structure is fabricated from a planar chip. The device can be micrometers wide and have a patterned surface created by the removal of material to a depth of, for example, tens of nanometers. As a specific example, a device having a quasi-2D structure can have a patterned surface depth (e.g., 30 nm) that is much smaller (e.g., 1000 times smaller) than its lateral size (e.g., 30 μm). A quasi-2D structure may use a progressive geometry (e.g., comprising a plurality of pillars with sizes and spacing selected to straighten the nucleic acid before it reaches the disintegrator). A 3D structure may use a funnel packed with spheres of different sizes in such a manner that the nucleic acid passing between spheres is straightened.

In some embodiments, the fluidic channel has a horizontal portion and a vertical portion, and the disintegrator is situated along the horizontal portion, and the nanopore is situated at the exit end of the vertical portion. This configuration can be convenient for manufacturability. For example, the horizontal and vertical portions of the fluidic channel can be etched into a substrate (e.g., silicon). A membrane can be attached to the back side of the substrate, and the nanopore can be created in the membrane at the exit end of the vertical portion of the channel (e.g., using dielectric breakdown). If the device includes a quasi-2D straightener, that straightener can be created at the same time the vertical and horizontal portions of the fluidic channel are created. If the device includes a 3D straightener, the funnel can be created at the same time the vertical and horizontal portions of the fluidic channel are created, and then it can be packed (e.g., with spheres) afterward. Alternatively, a 3D straightener can be fabricated separately and coupled to the fluidic channel.

The dimensions of the sequencing device, and particularly the distance between the disintegrator and the nanopore, can be selected to ensure that individual portions of the nucleic acid molecule (e.g., nucleotides) do not pass each other (i.e., their order is maintained) before being detected.

The disclosed devices, systems, and methods can be included in a data storage system that uses nanopores. Such systems are described, for example, in U.S. Patent Publication No. US 2023/0244412A1, which published on Aug. 3, 2023 and is hereby incorporated by reference in its entirety for all purposes. There are many applications for such data storage systems, ranging from archival storage of data intended to be stored and potentially never accessed again (e.g., except in an emergency) to data that is frequently written and read (e.g., on a personal computer). A data storage system using the disclosed devices, systems, and methods can comprise at least one processor communicatively coupled to read hardware and to a buffer (e.g., memory). In cooperation with the read hardware, the at least one processor can read molecules of the data storage system to retrieve data.

FIG. 1 illustrates a nanopore 15 with a molecule 20 (e.g., a single-stranded DNA (ssDNA) molecule), passing through it, where each circle represents a nucleotide. The nanopore 15 has an associated translocation direction 16, which is along the z-axis shown in FIG. 1, from an entry side of the nanopore 15 to an exit side of the nanopore 15. FIG. 1 shows the translocation direction 16 as being toward the bottom of the page, but it is to be appreciated that it could also (or alternatively) be in the opposite direction (toward the top of the page). Two sensing electrodes 18 (made from a suitable material, e.g., silver, platinum, etc.) are situated near the nanopore 15, on either side of it (e.g., on the entry side and on the exit side), to sense the ionic current through the nanopore 15. The sensing electrodes 18 are typically connected to a voltage source 30, which supplies a voltage to the sensing electrodes 18 and creates an electric potential across the nanopore 15. As explained above, as the molecule 20 passes through the nanopore 15, ions in the electrolyte solution are excluded from the hole in the nanopore 15, which causes changes in the ionic current and/or electronic signal measured across the nanopore 15 (e.g., using the sensing electrodes 18), which can be observed and used to detect constituent parts of the molecule 20 (e.g., nucleotides of a DNA strand). The sensing electrodes 18 may be coupled to detection circuitry (not illustrated) that detects the ionic current.

A challenge with using solid-state nanopores 15 for detection is that the thickness of the membrane in which the nanopores 15 are created is larger than the size of a single nucleotide. As a result, the ionic current measured is for multiple nucleotides (those within the nanopore 15 when the ionic current is measured). Although post-processing may be able to be used to resolve single nucleotides (e.g., by identifying patterns in the measured signal), it would be preferable to avoid having to perform such post-processing, which can be computationally intensive and could result in errors in the sequence.

Accordingly, one objective of the disclosures herein is to describe devices, systems, and methods to achieve single nucleotide sequencing using nanopores. In other words, one objective is to be able to detect the identities of single nucleotides (e.g., C, G, A, T for DNA; C, G, A, U for RNA; etc.) as they pass through a nanopore 15. In some embodiments, a disintegrator is embedded in a fluidic channel of a device so that when the nucleic acid encounters the disintegrator, a portion of the nucleic acid (e.g., a single nucleotide) is cleaved off the end of the nucleic acid polymer. That cleaved-off portion of the nucleic acid then passes through a nanopore 15 by itself, and its effect on the ionic current can be measured. To cause the individual portions of the nucleic acid (e.g., individual nucleotides) to pass through the nanopore 15, electrodes can be used to apply an electrostatic force that overcomes a hydrodynamic force in the device that might otherwise propel the portion of the nucleic acid along a path that does not include the nanopore 15.

It is to be appreciated that before being provided to the systems described herein and/or before applying the methods described herein, the nucleic acid polymer can be pre-conditioned, for example, to break up individual nucleic acids into smaller strands (e.g., less than about 1,000 bases) that should be less likely to clog the fluidic channel. Any suitable technique can be used for pre-conditioning (e.g., using restriction enzymes that recognize and bind to a specific DNA sequence to cleave DNA strands).

Figure 2A:
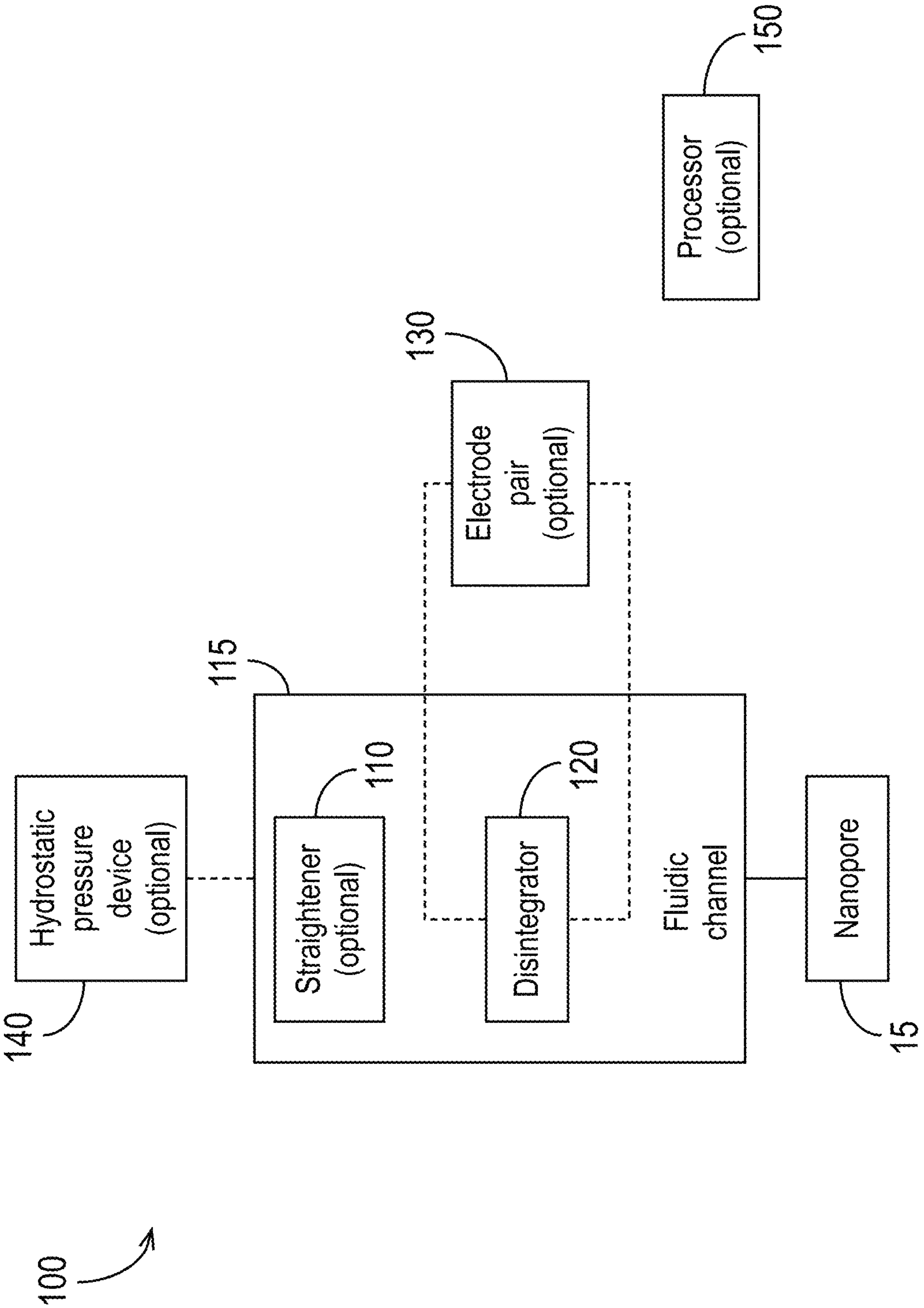
FIG. 2A is a diagram showing components of a system for single-nucleotide detection in accordance with some embodiments.

FIG. 2A is a high-level diagram showing components of a system 100 for single-nucleotide detection in accordance with some embodiments. As shown, the system 100 includes a fluidic channel 115. In the example shown in FIG. 2A, within the fluidic channel 115 are a straightener 110, which is optional, and a disintegrator 120. The fluidic channel 115 is coupled to a nanopore 15. The system 100 also includes an electrode pair 130, which is optional. As described below, if included, the electrodes of the electrode pair 130 are situated to apply a voltage that can be used to control the speeds of molecules through the disintegrator 120. Optionally, the system 100 includes a processor 150 (e.g., to control a voltage source coupled to the electrode pair 130, and/or to monitor the ionic current through the nanopore 15, and/or to perform assembly/stitching, etc.).

Optionally, the system 100 includes a hydrostatic pressure device 140 coupled to the fluidic channel 115 to control (or help control) the speed of the molecule 20 through the disintegrator 120, as described further below. If present, the hydrostatic pressure device 140 may comprise any suitable system or device that can apply hydrostatic pressure to the fluidic channel 115. The hydrostatic pressure device 140 can have both an inlet or an outlet (e.g., such that the hydrostatic pressure device 140 conveys fluid from a tank or reservoir coupled to the inlet of the hydrostatic pressure device 140 to a fluidic channel 115 coupled to the outlet of the hydrostatic pressure device 140), or it can have only an outlet (e.g., the hydrostatic pressure device 140 stores fluid and delivers fluid to an inlet of the fluidic channel 115 via the outlet of the hydrostatic pressure device 140), or it can have only an inlet (e.g., the hydrostatic pressure device 140 pulls fluid out of the fluidic channel 115 via the inlet of the hydrostatic pressure device 140 and into a tank or reservoir of the hydrostatic pressure device 140).

In some embodiments, the hydrostatic pressure device 140 comprises a vessel that is configured to store pressurized liquid (e.g. using a liquid and a gas chamber separated by a membrane or piston, or using an elastic housing). As an example, the hydrostatic pressure device 140 can be or comprise a hydraulic accumulator (e.g., a device that can indirectly apply hydrostatic pressure by releasing stored hydraulic energy when needed). As specific examples, the hydrostatic pressure device 140 can be or comprise a pressure accumulator, a bladder-type accumulator, a membrane-type accumulator, an accumulator using pistons, an accumulator having springs, or other similar devices. Alternatively or in addition, the hydrostatic pressure device 140 can be or comprise a pressure pump (e.g., a reciprocating plunger pump or any device or system that can move fluid from a tank into the fluidic channel 115). As another example, the hydrostatic pressure device 140 can be or comprise a reservoir containing a liquid, such that raising or lowering the level of liquid within the reservoir applies hydrostatic pressure to the fluidic channel 115. As yet another example, the hydrostatic pressure device 140 can be or comprise a device that operates similarly to a water tower of a municipal water distribution system (e.g., using hydrostatic pressure and/or gravity to supply consistent water pressure to homes and businesses). If present, the hydrostatic pressure device 140 can be situated in any suitable location. For example, it can be situated at an inlet of the fluidic channel 115, at an outlet of the fluidic channel 115, downstream of the straightener 110 (if included), downstream of the disintegrator 120, etc. As explained above, the hydrostatic pressure device 140 can include a fluid reservoir, vessel, or tank. Alternatively or in addition, the hydrostatic pressure device 140 can be coupled to a fluid reservoir, vessel, or tank.

As described further below, if included, the straightener 110 operates to straighten a molecule prior to it being handled by the disintegrator 120. For example, it is known that ssDNA can fold over on itself, forming secondary structures (e.g., hairpin loops, stem-loop structures, G-quadruplex structures, pseudoknots, etc.) that may be stabilized by base-pairing interactions between complementary nucleotide sequences within the same ssDNA molecule. Accordingly, in some embodiments, the straightener 110 is provided to reduce and/or remove these secondary structures (or prevent them from occurring while the nucleic acid is in the fluidic channel 115) by straightening the nucleic acid polymer before it reaches the disintegrator 120.

Although FIG. 2A shows the straightener 110 and the disintegrator 120 as being within the fluidic channel 115, it is possible for the straightener 110 and/or the disintegrator 120 to be separate components that are coupled to the fluidic channel 115.

Figure 2B:
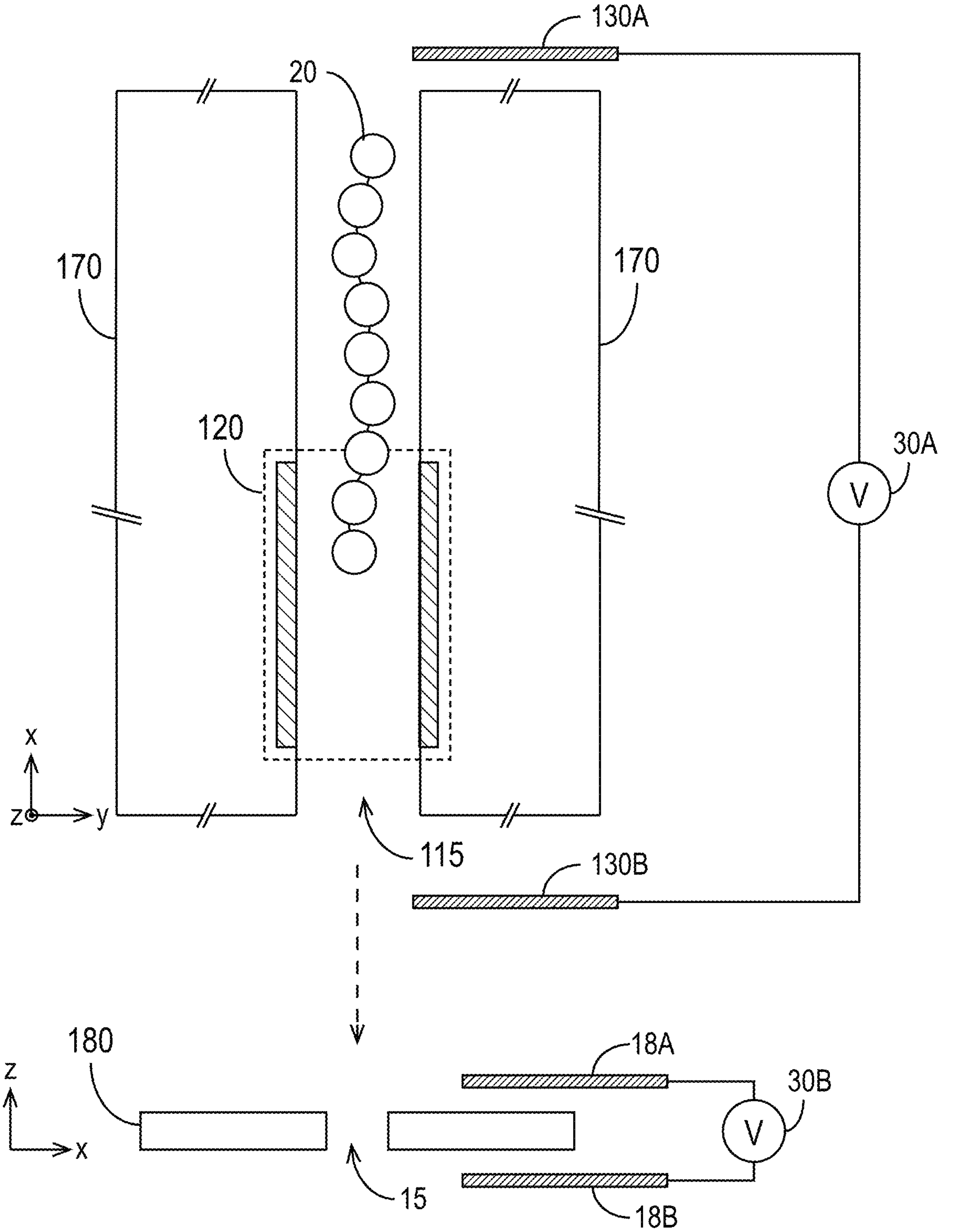
FIG. 2B is a diagram showing a configuration of electrodes in accordance with some embodiments.

FIG. 2B is a diagram showing a configuration of electrodes for controlling the translocation of the molecule 20 into the disintegrator 120, for applying an electrostatic force to direct the cleaved-off portions of the nucleic acid (e.g., single nucleotides) into the nanopore 15, and for sensing the ionic current through the nanopore 15 in accordance with some embodiments. As shown, an electrode 130A and an electrode 130B of the electrode pair 130, which are coupled to a voltage source 30A, are situated where they can be used to control the translocation of the molecule 20 into the disintegrator 120. The sensing electrode 18A and the sensing electrode 18B, which are coupled to a voltage source 30B, apply an electrostatic force that can direct portions of the nucleic acid (illustrated in FIG. 2B as single nucleotides 25) cleaved from the molecule 20 by the disintegrator 120 into the nanopore 15. The sensing electrode 18A and sensing electrode 18B can also detect ionic currents through the nanopore 15 as described above in the context of FIG. 1. As shown and described below, the electrode 130A and the electrode 130B can be situated in the fluidic channel 115. Because the voltages of the voltage source 30A and the voltage source 30B can be set/controlled independently, the speed of the molecule 20 through the disintegrator 120 can be controlled independently of the electrostatic force applied to divert the cleaved-off portion of the nucleic acid (e.g., nucleotide 25) through the nanopore 15.

It is to be appreciated that the electrode 130A and the electrode 130B are optional. As an alternative or additional mechanism to control the speed of the molecule 20 through the disintegrator 120, hydrostatic pressure (e.g., due to a hydrostatic pressure device 140, as shown in FIG. 2A and described above) can be used. Thus, the speed of a molecule 20 through the disintegrator 120 can be controlled by (a) the electrode 130A and electrode 130B, and/or (b) hydrostatic pressure applied by, for example, a hydrostatic pressure device 140 coupled to the fluidic channel 115.

FIG. 2B shows four electrodes (namely, electrode 130A, electrode 130B, sensing electrode 18A, and sensing electrode 18B), but it is to be appreciated that adjacent electrodes could be combined. For example, referring to FIG. 2B, the electrode 130B and sensing electrode 18A could be combined into a single electrode that would be coupled to both the voltage source 30A and the voltage source 30B.

Figure 3A:
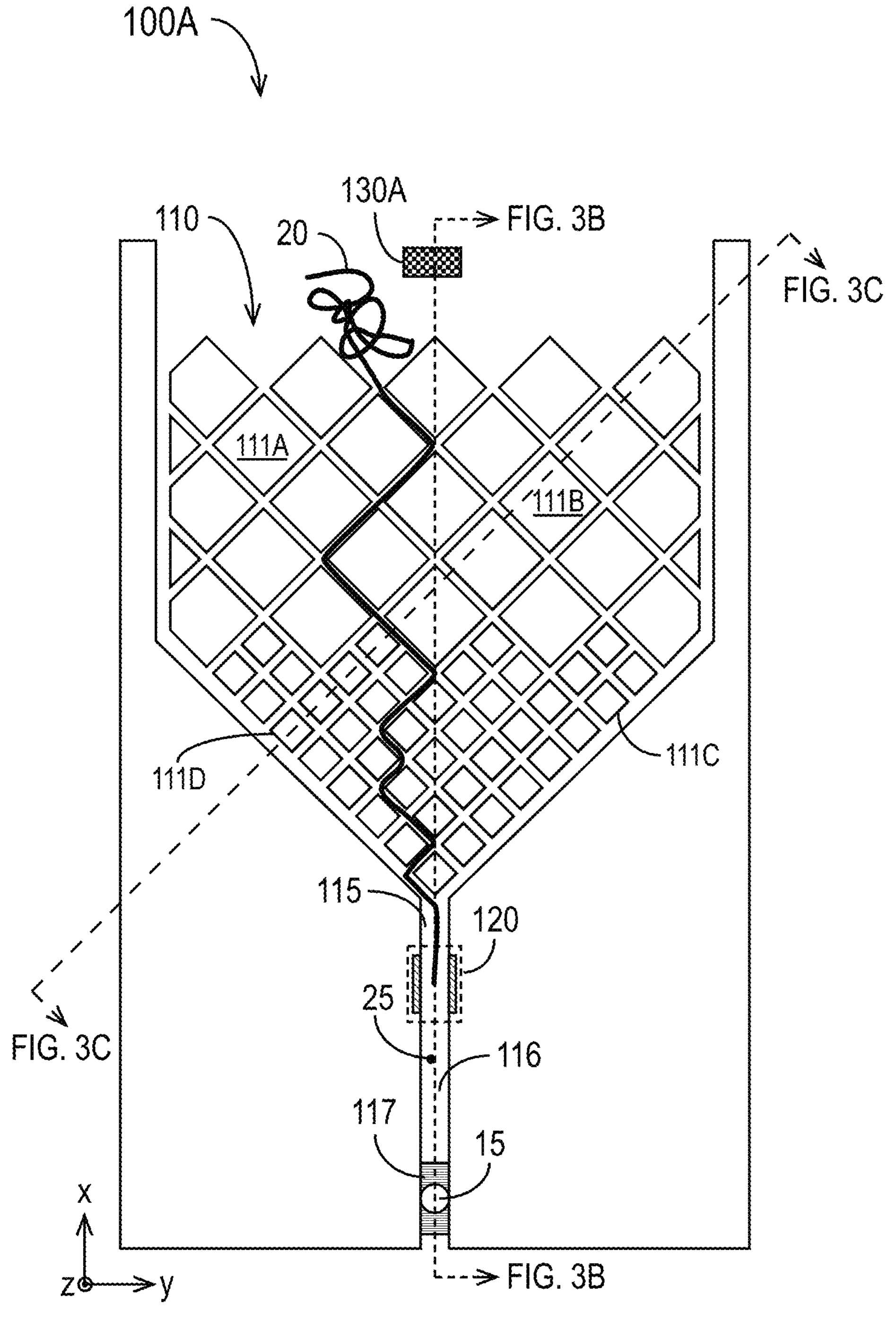
FIGS. 3A, 3B, and 3C illustrate an example of a device for performing single-nucleotide sequencing in accordance with some embodiments.
Figure 3B:
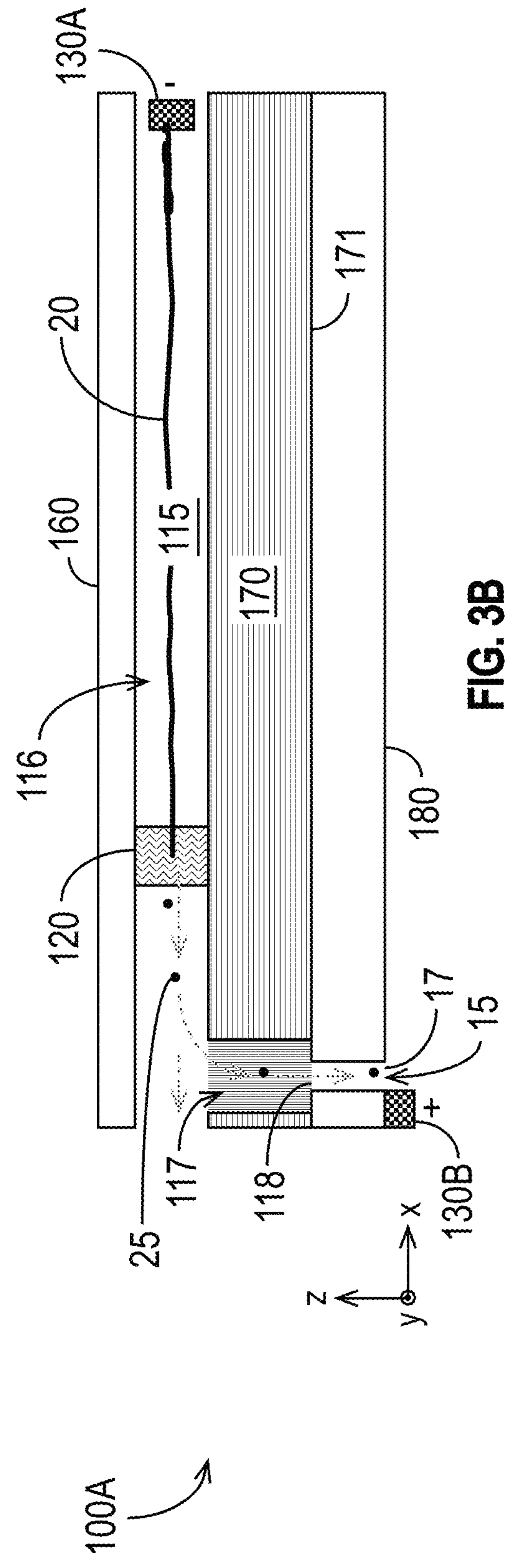
Figure 3C:
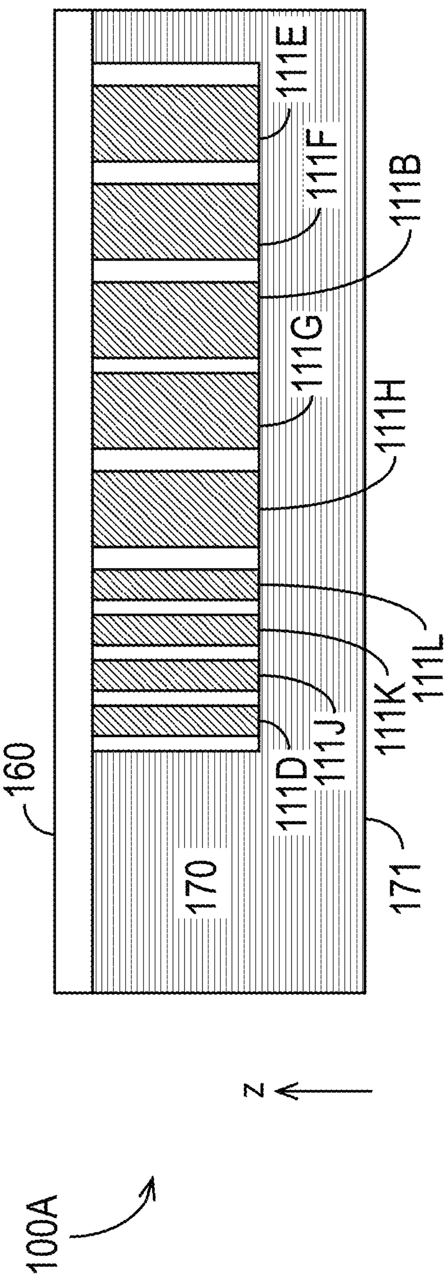

FIGS. 3A, 3B, and 3C illustrate an example of a device 100A for performing single-nucleotide sequencing in accordance with some embodiments. FIG. 3A is a top view of the device 100A, FIG. 3B is a cross-section view of the device 100A along the vertical dashed line shown and labeled in FIG. 3A, and FIG. 3C is a cross-section view of the device 100A along the diagonally-oriented dashed line shown and labeled in FIG. 3A. To avoid obscuring the drawing, FIG. 3B does not show the pillars 111 of the straightener 110, described further below. In other words, the view shown in FIG. 3B is the view assuming the pillars 111 are transparent so that the molecule 20 is visible along the length of the horizontal portion 116 of the fluidic channel 115.

FIGS. 3A, 3B, and 3C include axes for reference. For ease of explanation, in this document, the x-y plane is considered to be a horizontal plane, and the z-direction is vertical. The view of FIG. 3A is in an x-y plane (a top view of the device 100A). The view of FIG. 3B is in an x-z plane. The view in FIG. 3C is in a vertical plane that is at an angle to both the x-axis and the y-axis in FIG. 3A.

Referring to FIGS. 3A, 3B, and 3C, the device 100A includes a straightener 110 (optional), a disintegrator 120, a fluidic channel 115, an electrode 130A, an electrode 130B, a cover 160, a substrate 170, and a membrane 180 with a nanopore 15. (To avoid cluttering the drawings, the sensing electrodes 18 and voltage source 30 of FIG. 1 are not specifically illustrated in FIG. 3A, 3B, 3C, or subsequent drawings herein, but it is to be appreciated that these components are present.) With the defined coordinate system in which the z-axis is vertical, the fluidic channel 115 has a horizontal portion 116 and a vertical portion 117. In the example of the device 100A shown in FIGS. 3A, 3B, and 3C, the disintegrator 120 is situated along the horizontal portion 116 of the fluidic channel 115, and the vertical portion 117 extends through the substrate 170. The membrane 180 is situated on the back side 171 of the substrate 170. The nanopore 15 in the membrane 180 is situated at an exit end 118 of the vertical portion 117 of the fluidic channel 115. The cleaved-off portion of the nucleic acid (e.g., nucleotide 25) exits the nanopore 15 via the exit side 17 of the nanopore 15.

The cover 160 can be, for example, a coverslip. In some embodiments, the cover 160 has good transparency and thermal and chemical resistance. For example, the cover 160 can be floated borosilicate glass, such as, for example, a 170 micron Borofloat® 33 made by Schott. The cover 160 may be removable. The cover 160 may cause fluid within the fluidic channel 115 to be subjected to hydrostatic pressure that pulls the molecule 20 in the negative-x direction (for FIG. 3A, downward on the page, and for FIG. 3B, to the left).

The electrode 130A and the electrode 130B are configured to exert an electrostatic force on the molecule 20 as it proceeds to the disintegrator 120 and on a cleaved-off portion of the molecule 20 (e.g., nucleotide 25) as the portion (e.g., nucleotide 25) proceeds from the disintegrator 120 through the remainder of the fluidic channel 115. In the example of FIG. 3B, individual nucleotides 25 are cleaved from the molecule, the electrode 130A is negative, and the electrode 130B is positive so that when the voltage is applied to the electrode 130A and the electrode 130B, the negatively-charged nucleotide 25 is attracted to the electrode 130B. Thus, the electrostatic force causes the nucleotide 25 to be diverted from the horizontal portion 116 of the fluidic channel 115 and to proceed through the vertical portion 117 and the nanopore 15. To cause the nucleotide 25 to enter the vertical portion 117 of the fluidic channel 115 and the nanopore 15, the electrostatic force exerted by the electrode 130A and the electrode 130B should be larger than the hydrodynamic force on the nucleotide 25 due to the applied hydrostatic pressure and fluid flow. As explained above, the electrode 130B can be one of the sensing electrodes 18 of the nanopore 15.

The substrate 170 can be any suitable material. For example, the substrate 170 can be made from or comprise silicon, glass, polymer, etc.

The membrane 180 may be made of any suitable material. For example, the membrane 180 may be made from silicon dioxide ($SiO_2$), silicon nitride ($Si_3N_4$), or polymer materials such as polyethylene. As described further below, the nanopore 15 may be created in the membrane 180. The membrane 180 may cover all of the back surface of the substrate 170, or it may cover only part of the back surface of the substrate 170 (e.g., the region around where the nanopore 15 is located). In some embodiments, the membrane 180 is a locally-thinned portion of a second substrate. FIG. 3B shows the membrane 180 covering the back surface of the substrate 170 at least along the entirety of the dashed line of FIG. 3A. FIG. 3C shows the cross-section view assuming that the membrane 180 does not cover the entire back surface of the substrate 170 and therefore is not visible in the cross section along the "FIG. 3C" dashed line shown in FIG. 3A (e.g., there may be a strip of membrane on the back side 171 of the substrate 170).

If the optional straightener 110 is included, it can use any structure or combination of structures that encourage the nucleic acid polymer to linearize as it progresses through the device 100A. In the example shown in FIGS. 3A and 3C, the straightener 110 is a quasi-2D straightener that comprises pillars 111. The pillars 111 are arranged in a configuration that results in the molecule 20 being linearized as it passes through the straightener 110. The device 100A can have any number of pillars 111. To avoid obscuring the drawing, only four pillars are labeled in FIG. 3A, namely the pillar 111A, the pillar 111B, the pillar 111C, and the pillar 111D. FIG. 3C is a cross-section view that shows additional pillars 111 of the device 100A example. Specifically, FIG. 3C shows cross-sections of the pillar 111B, the pillar 111D, and seven other pillars 111, namely the pillar 111J, the pillar 111K, the pillar 111L, the pillar 111H, the pillar 111G, the pillar 111E, and the pillar 111F. As shown in FIG. 3C, the pillars 111 can extend in the z-direction to contact the cover 160 so that the molecule 20 cannot become lodged (stuck) between the tops of the pillars 111 and the cover 160.

As shown in FIGS. 3A and 3C, different pillars 111 can have different sizes. For example, the sizes of the pillars 111 can decrease closer to the disintegrator 120. Although FIG. 3A shows only two sizes and one shape for the pillars 111, it is to be appreciated that there can be more variation in sizes and/or shapes. Alternatively, all pillars 111 can be the same size and shape.

Although FIGS. 3A and 3C show the spacing between adjacent pillars 111 as being approximately the same throughout the straightener, consistent spacing is not a requirement. For example, a straightener 110 with pillars 111 may have different spacings between adjacent pillars 111. As a specific example, adjacent pillars 111 of the straightener 110 that are closer to the disintegrator 120 may be closer to each other than adjacent pillars 111 that are further away from the disintegrator 120. Thus, the spacing between pillars 111 can change as the distance between the pillars 111 and the disintegrator 120 changes (e.g., the spacing can generally decrease as the distance from the disintegrator 120 decreases). Varying the sizes of and spacing between pillars 111 can encourage the nucleic acid to become linearized as it traverses the straightener 110.

As an example, the straightener 110 can have a progressive geometry in which both the size of the pillars 111 and the gaps between adjacent pillars 111 decrease for smaller values along the x-axis shown in FIG. 3A. The use of a progressive geometry may help linearize the nucleic acid and/or prevent clogging. For example, at the largest x values of the straightener 110, the pillars 111 and gaps between adjacent pillars 111 can be at their largest values, and at the smallest x values of the straightener 110, the pillars 111 and gaps between adjacent pillars 111 can be at their smallest values. Once a progressive geometry configuration has been determined, clogging can be monitored (e.g., via modeling or in an implementation) to refine the physical characteristics of the straightener 110. If clogging is observed, the progressive geometry can be modified and/or refined (e.g., gaps can be reduced, additional pillars 111 can be added, the size(s) and/or shape(s) of pillars 111 can be modified, etc.).

Figure 4A:
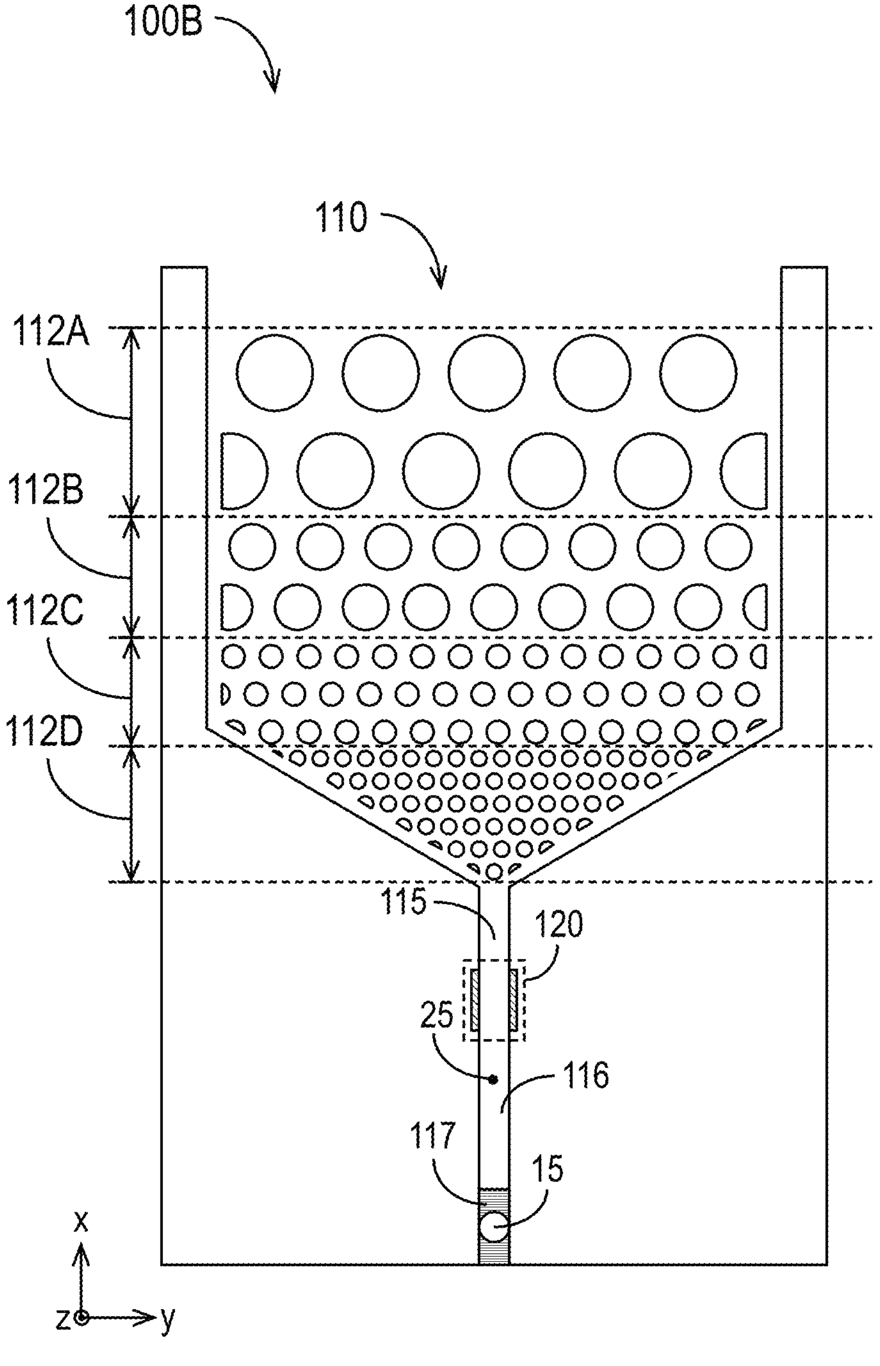
FIG. 4A illustrates an example of a device that has a straightener with a progressive geometry structure in accordance with some embodiments.

As a specific example, FIG. 4A illustrates an example of a device 100B that has a straightener 110 with a progressive geometry structure in which both the size of the pillars 111 and the spacing between adjacent pillars 111 decrease as the value of x decreases, in accordance with some embodiments. FIG. 4A also shows other components of the device 100B that were described and illustrated above in the context of FIGS. 3A, 3B, and 3C. Except with respect to the differences in the straightener 110, those descriptions also apply here and are not repeated. Specifically, at least the descriptions of FIGS. 3B and 3C apply to the device 100B shown in FIG. 4A.

The example of FIG. 4A includes bands 112 of pillars 111, namely the band 112A, the band 112B, the band 112C, and the band 112D. The band 112A of pillars 111 is furthest away from the disintegrator 120. As compared to the other bands 112, the pillars 111 in the band 112A are of the largest size, and the gaps between adjacent pillars 111 in the band 112A are the largest. The pillars 111 in the band 112B are smaller than the pillars 111 in the band 112A, and adjacent pillars 111 in the band 112B are separated by smaller gaps than the pillars 111 in the band 112A. The pillars 111 in the band 112C are smaller than the pillars 111 in the band 112B, and adjacent pillars 111 in the band 112C are separated by smaller gaps than the pillars 111 in the band 112B. The pillars 111 in the band 112D are the smallest, and the gaps between adjacent pillars in the band 112D are the smallest of all of the bands 112.

Figure 4B:
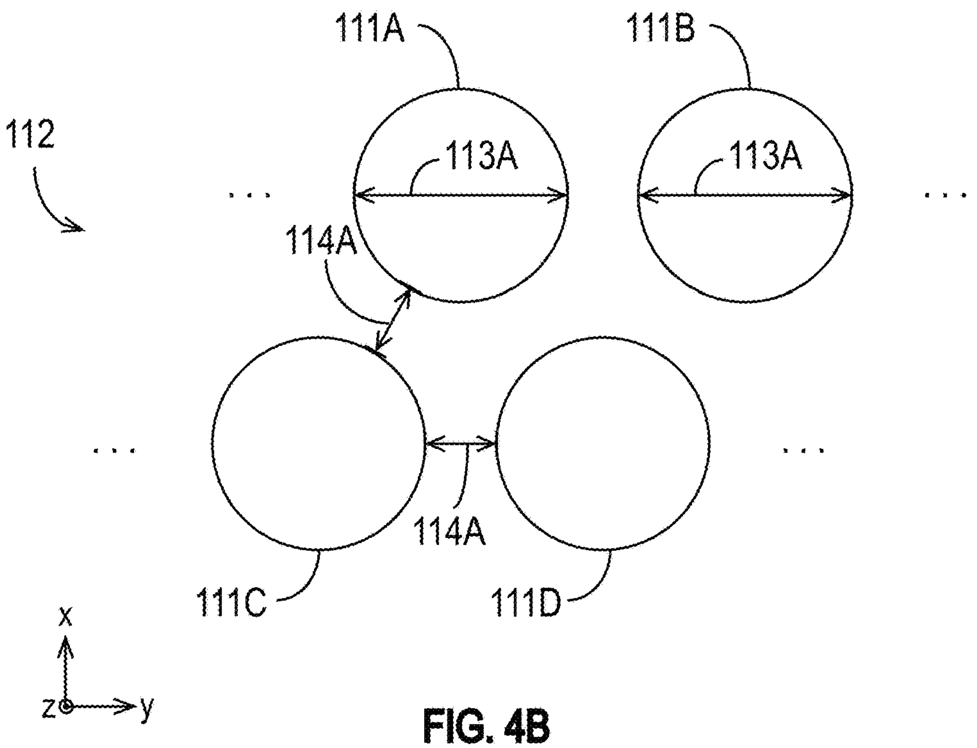
FIG. 4B is a closer view of four examples of pillars in a band in accordance with some embodiments.

FIG. 4B is a closer view of four examples of pillars 111 in a band 112, namely a pillar 111A, a pillar 111B, a pillar 111C, and a pillar 111D. The illustrated pillars 111 could be situated in any of the band 112A, band 112B, band 112C, or band 112D. Each of the pillar 111A, pillar 111B, pillar 111C, and pillar 111D has a diameter 113A, which, in the illustrated example, is the same value for all of the pillars 111 within the band 112. The minimum distance between adjacent pillars 111 (the gap) is a minimum distance 114A. In the illustrated example, the minimum distance 114A between adjacent pillars 111 is the same for all of the pillars 111 in the band 112.

Figure 4C:
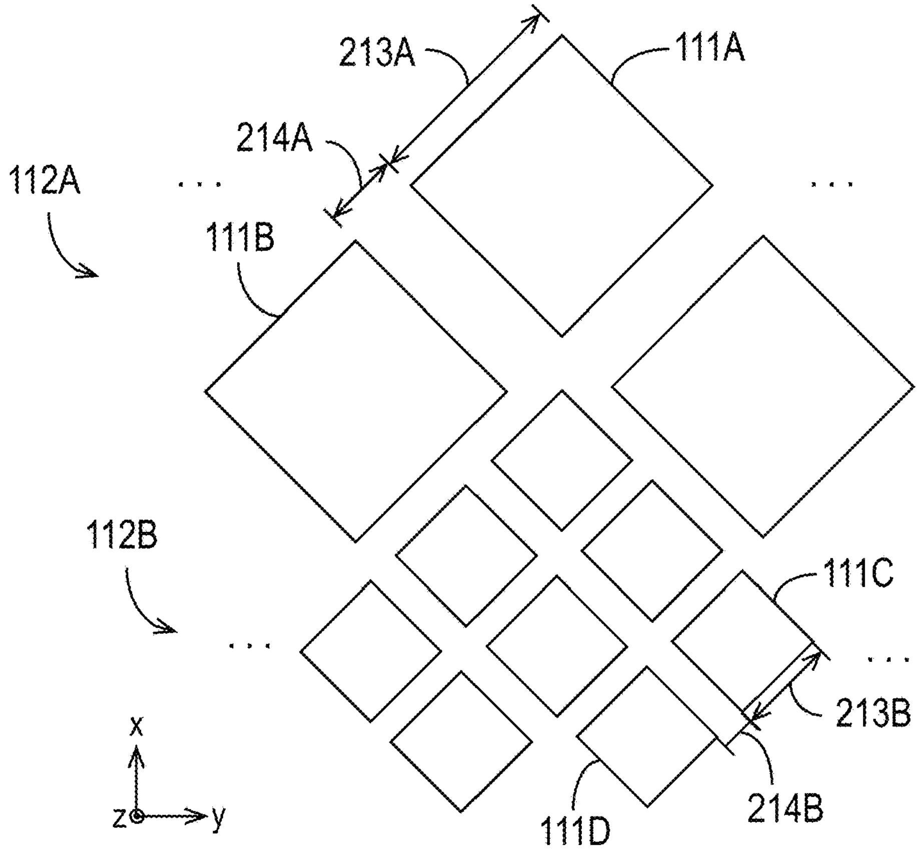
FIG. 4C shows a portion of a configuration of a straightener that has at least two bands in which the pillars are cuboid in accordance with some embodiments.

FIG. 4A illustrates a progressive geometry using cylindrical pillars 111, and FIG. 4B also shows cylindrical pillars 111, but it is to be appreciated that other shapes are possible (e.g., cuboid, prisms, etc.). For example, FIG. 4C shows a portion of a configuration of a straightener 110 that has at least two bands 112 in which the pillars 111 are cuboid. Four of the pillars 111 are labeled in FIG. 4C, namely the pillar 111A, the pillar 111B, the pillar 111C, and the pillar 111D. Similarly, portions of two bands 112 are shown, namely the band 112A and the band 112B. In the example configuration of FIG. 4C, the pillars 111 have a square shape in the x-y plane. In the band 112A, each side of the pillars 111 has a length 213A in the x-y plane, and adjacent pillars 111 are separated by a minimum distance 214A within the band 112A. In the band 112B, each side of the pillars 111 has a length 213B in the x-y plane, and adjacent pillars 111 are separated by a minimum distance 214B within the band 112B. As shown, the length 213A is larger than the length 213B, and the minimum distance 214A is larger than the minimum distance 214B. A straightener 110 may include additional pillars 111 and/or additional bands 112.

The sizes of the pillars 111 (e.g., diameter, edge length, etc.) and the minimum distance (e.g., minimum distance 114A, minimum distance 214A, minimum distance 214B, etc.) between adjacent pillars 111 within the different bands 112 can be any suitable values. For example, with reference to FIG. 4C, the length 213A in the band 112A can be 6-7 microns, and the minimum distance 214A can be 1-2 microns. The length 213B in the band 112B can be 3-4 microns, and the minimum distance 214B can be 0.5-1 micron. As noted above in the discussion of FIG. 4A, the configuration for a straightener 110 can include additional bands 112. Cuboid pillars 111 in the band 112C could have, for example, a length of 1-2 microns and a minimum distance of 0.2-0.5 microns. The pillars 111 in the band 112D could have, for example, a length less than or equal to 1 micron and a minimum distance less than 0.2 microns. It will be appreciated that the values provided above are merely examples, and that other choices are possible.

Also, it is to be appreciated that the bands 112 need not be in a horizontal configuration ("stripes") as shown in FIG. 4A. For example, the bands 112 could be in "v" shapes (e.g., as shown in FIG. 4C), or they could be in zig-zag shapes. Designing an appropriate geometry of pillars 111 for a straightener 110 is well within the level of ordinary skill based on the disclosures herein.

In embodiments in which the straightener 110 includes pillars 111, the pillars 111 can have any shape and/or size. For example, the pillars 111 can be cylindrical (e.g., circular or oval cylinders) as shown in FIGS. 4A and 4B. As another example, the pillars 111 can be cuboid (e.g., as shown in FIGS. 3A and 4C). Similarly, the straightener 110 can include a mix of pillars 111 having different shapes (e.g., some can be cuboid, some can be circular cylinders, some can be oval cylinders, some can be prisms, etc.). The examples provided herein are not intended to be limiting. In general, a straightener 110 could have any number of bands 112 and any number of pillars 111, and the physical characteristics (e.g., size, shape, number, etc.) and positions (e.g., pattern, minimum distance, etc.) of the pillars 111 and the bands 112 can be determined using the principles disclosed herein.

The examples of the straightener 110 shown in FIGS. 3A, 3C, 4A, 4B, and 4C are what may be referred to as "quasi-two-dimensional" or "quasi-2D" approaches in which the straightener 110 comprises a structure (or structures) configured to cause movement of the molecule 20 to be substantially planar (e.g., the molecule 20 can move in an x-y plane through the straightener 110, but the straightener 110 allows little or no movement in the z-direction). In some such approaches, the width of the fluidic channel 115 decreases monotonically as the distance from the nanopore 15 decreases. For example, using the coordinate system shown in FIG. 3A, the width, which is in the y-direction, decreases monotonically as the value of x decreases. In some embodiments, the width of the fluidic channel 115 decreases from micron scale to nanometer scale.

Figure 4D:
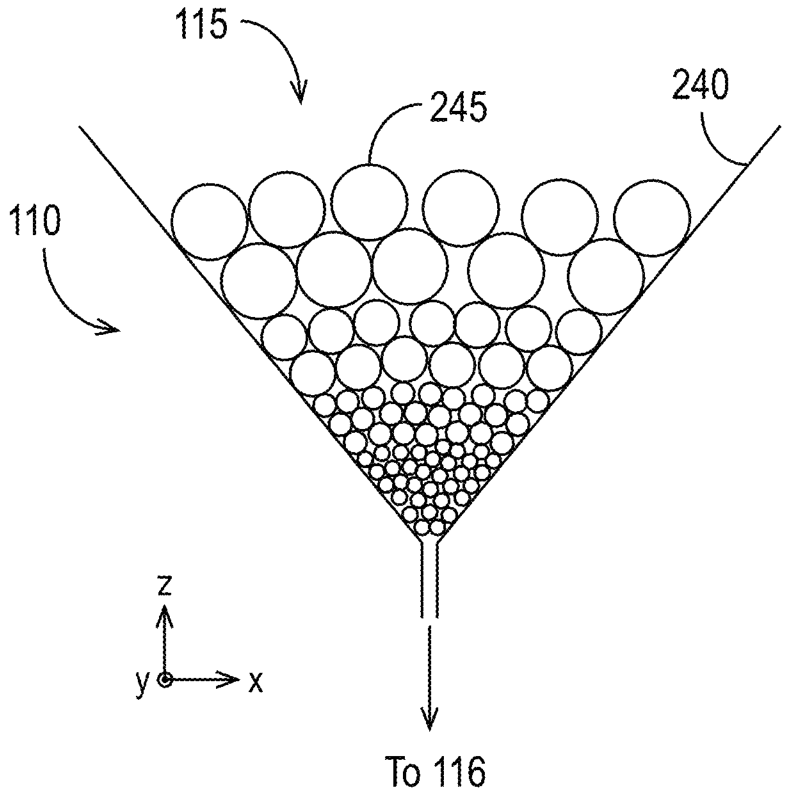
FIG. 4D illustrates an example of a straightener that uses a funnel in accordance with some embodiments.

Another approach for the straightener 110 is to use a three-dimensional (3D) approach in which the straightener 110 includes a three-dimensional structure (or structures) configured to allow the molecule 20 to move in three-dimensions while being straightened. For example, the fluidic channel 115 can include a vertically-oriented funnel. The straightener 110 can comprise structures inside of the funnel that cause the molecule 20 to be straightened as it flows through the funnel. FIG. 4D illustrates an example cross-section of a straightener 110 that uses a funnel in accordance with some embodiments. As shown, the fluidic channel 115 includes a vertically-oriented funnel 240, which may be at micron scale. In the illustrated example, the vertically-oriented funnel 240 is packed with spheres 245. The spheres 245 at the narrowest (bottom, exit) portion of the vertically-oriented funnel 240 are the smallest, and the spheres 245 at the widest (top, entrance) part of the vertically-oriented funnel 240 are the largest. The spheres 245 provide multiple paths through the vertically-oriented funnel 240, and these paths allow the nucleic acid polymers to flow through the vertically-oriented funnel 240 and be linearized as they approach the exit of the vertically-oriented funnel 240, thereby mitigating clogging.

As noted above, the use of the straightener 110 is optional. In embodiments in which the system (e.g., the system 100) or device (e.g., device 100A, device 100B, etc.) does not include a straightener 110, the nucleic acid can pass directly from a bath into the fluidic channel 115. The size and/or shape of the fluidic channel 115 can be the same as shown in FIGS. 3A and 4A, or the size and/or shape of the fluidic channel 115 can be different when the straightener 110 is not included. The nucleic acid can be pre-conditioned to mitigate clogging (e.g., to reduce the length of nucleic acid strands to be no longer than some number of bases) when a straightener 110 is not included.

The disintegrator 120 operates to cleave off portions (e.g., single nucleotides) from a molecule traversing the system 100. In some embodiments, the disintegrator 120 is embedded in the fluidic channel 115 (e.g., in the walls along the horizontal portion 116 of the fluidic channel 115).

One challenge for the disintegrator 120 is to restrict disintegration to single phosphodiester bonds to cleave single nucleotides despite that neighboring phosphodiester bonds are separated by only five other chemical bonds and span only about one-third of a nanometer. The disintegrator 120 can use any suitable technique to cleave off portions (e.g., single nucleotides) of the molecule. For example, the disintegrator 120 can use enzymatic cleavage techniques, such as exonucleases. Exonucleases are enzymes that cleave nucleotides from the ends of nucleic acid molecules. For instance, exonuclease I cleaves single nucleotides from 3' end of DNA, while exonuclease III cleaves from 3' end of DNA but can also remove a few nucleotides from the 5' end.

As another example, the disintegrator 120 can use base-specific cleavage. For example, certain chemicals (e.g., hydrazine or osmium tetroxide) can be used to specifically cleave at specific bases (e.g., adenine or guanine). Base-specific cleavage can be used by the disintegrator 120 to selectively remove individual bases from a nucleic acid molecule.

In some embodiments, the disintegrator 120 uses a catalytic moiety embedded in the fluidic channel 115 (e.g., in walls of the horizontal portion 116) to cleave off portions (e.g., single nucleotides 25) of nucleic acids traversing the fluidic channel 115. In some embodiments, the catalytic moiety comprises divalent cations. As will be appreciated by those having ordinary skill in the art, a divalent cation is an ion with a positive charge of +2 that is formed when an atom or ion loses two electrons. Divalent cations are often associated with the elements found in Group 2 of the periodic table, known as the alkaline earth metals. Divalent cations can act as Lewis acids, meaning they can accept pairs of electrons, and they can form coordination complexes with other molecules or ions.

Any suitable divalent cations can be generated and/or used by (or as) the disintegrator 120 (e.g., embedded in the walls of the horizontal portion 116 of the fluidic channel 115). For example, the divalent cations may comprise magnesium ($Mg^{2+}$), cadmium ($Cd^{2+}$), calcium ($Ca^{2+}$), barium ($Ba^{2+}$), strontium ($Sr^{2+}$), and/or zinc ($Zn^{2+}$). Alternatively or in addition, metal ion compounds that contain divalent cations could be used, for example, one or more of: magnesium chloride ($MgCl_2$), calcium chloride ($CaCl_2$)), manganese chloride ($MnCl_2$), copper (II) chloride ($CuCl_2$), zinc chloride ($ZnCl_2$), cobalt (II) chloride ($CoCl_2$), cadmium chloride ($CdCl_2$), barium chloride ($BaCl_2$), strontium chloride ($SrCl_2$), ytterbium chloride ($YbCl_2$), nickel chloride ($NiCl_2$), lead chloride ($PbCl_2$), silver nitrate ($AgNO_3$), mercury (II) cyanide ($Hg(CN)_2$)), and/or potassium tetrachloroplatinate (II) ($K_2PtCl_4$).

As another example, the disintegrator 120 can use reactive oxygen species (ROS) (e.g., in addition to divalent cations) to perform hydrolysis on phosphodiester bonds in a nucleic acid (e.g., a DNA polymer). As will be appreciated, ROS are chemically-reactive molecules containing oxygen that are formed as natural byproducts of various metabolic processes. One way to create ROS and divalent cations is by using electrolysis. As will be appreciated, electrolysis is a chemical process that uses an electric current to drive a non-spontaneous chemical reaction, leading to the decomposition or formation of chemical substances. Electrolysis involves the splitting of a compound into its constituent elements or ions through the application of an electric voltage. Electrolysis uses an electrolyte and electrodes (namely, a cathode, and an anode). The electrolyte is a substance that can conduct electricity when dissolved in a solvent (e.g., water). The electrolyte contains ions that can migrate toward the electrodes. The cathode is connected to the negative terminal of a power source (e.g., a battery or power supply), and the anode is connected to the positive terminal of the power source. When an electric current flows through the electrolyte, it induces chemical reactions at the electrodes. Electrons flow from the anode to the cathode through an external circuit, and ions in the electrolyte move toward the oppositely charged electrodes. At the cathode, reduction reactions occur where positively charged ions (cations) gain electrons and are reduced to form neutral atoms or molecules. At the anode, oxidation reactions take place, where negatively charged ions (anions) lose electrons and are oxidized to form neutral atoms or molecules. These reactions are driven by the electrical potential difference between the electrodes. The chemical reactions that occur during electrolysis depend on the type of electrolyte and the substances present.

Figure 5A:
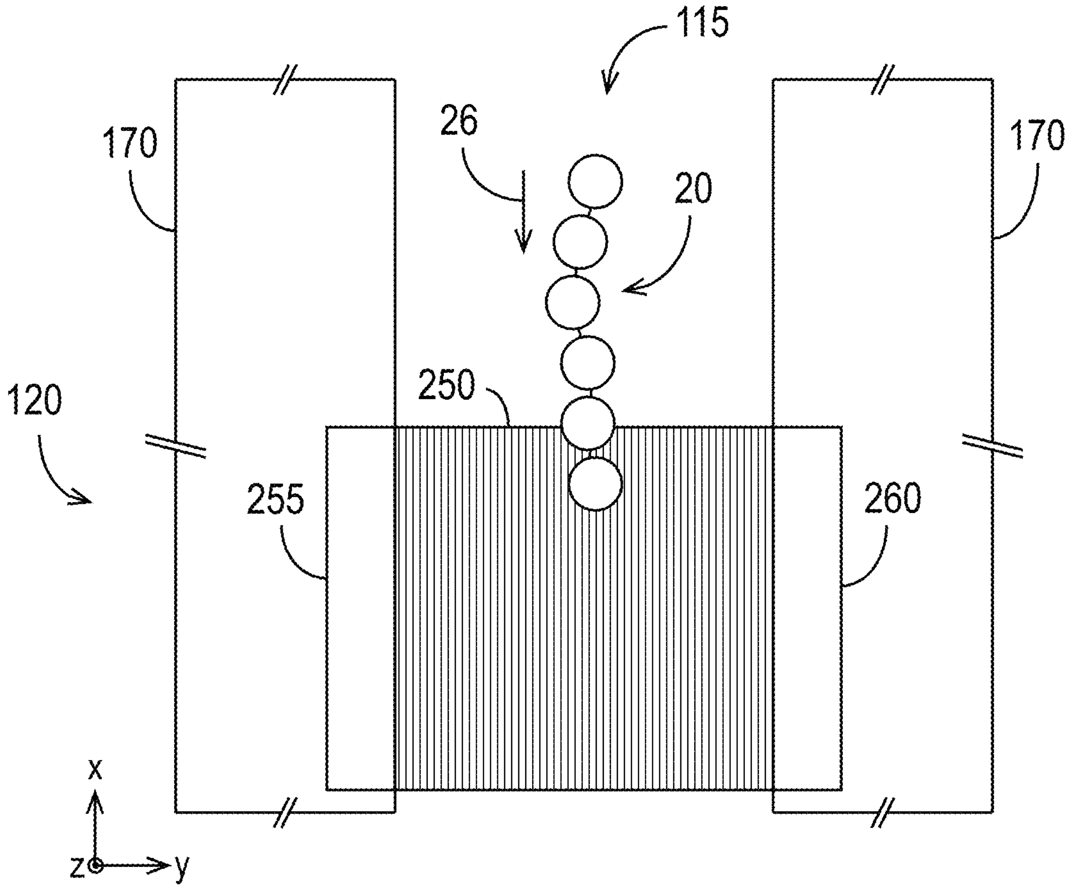
FIG. 5A is a diagram showing one way the disintegrator can create reactive oxygen species in addition to divalent cations using electrolysis in accordance with some embodiments.

FIG. 5A is a diagram showing one way the disintegrator 120 can create ROS in addition to divalent cations by electrolysis with an electric potential on a thin wire 250 situated substantially perpendicular to the direction 26 in which the nucleic acid (e.g., the molecule 20) moves through the fluidic channel 115. In the example of FIG. 5A, the disintegrator 120 includes a thin wire 250 coupled to a cathode 255 and an anode 260. As explained above, the cathode 255 and anode 260 are coupled to a power source (e.g., a battery), not illustrated in FIG. 5A. In the illustrated example, the thin wire 250 is not required to be exposed to the molecule 20 in solution. For example, the ROS can be created at the surfaces of the cathode 255 and the anode 260. If the thin wire 250 serves as a heater, as explained further below, the thin wire 250 could be exposed to the molecule 20 in solution.

Figure 5B:
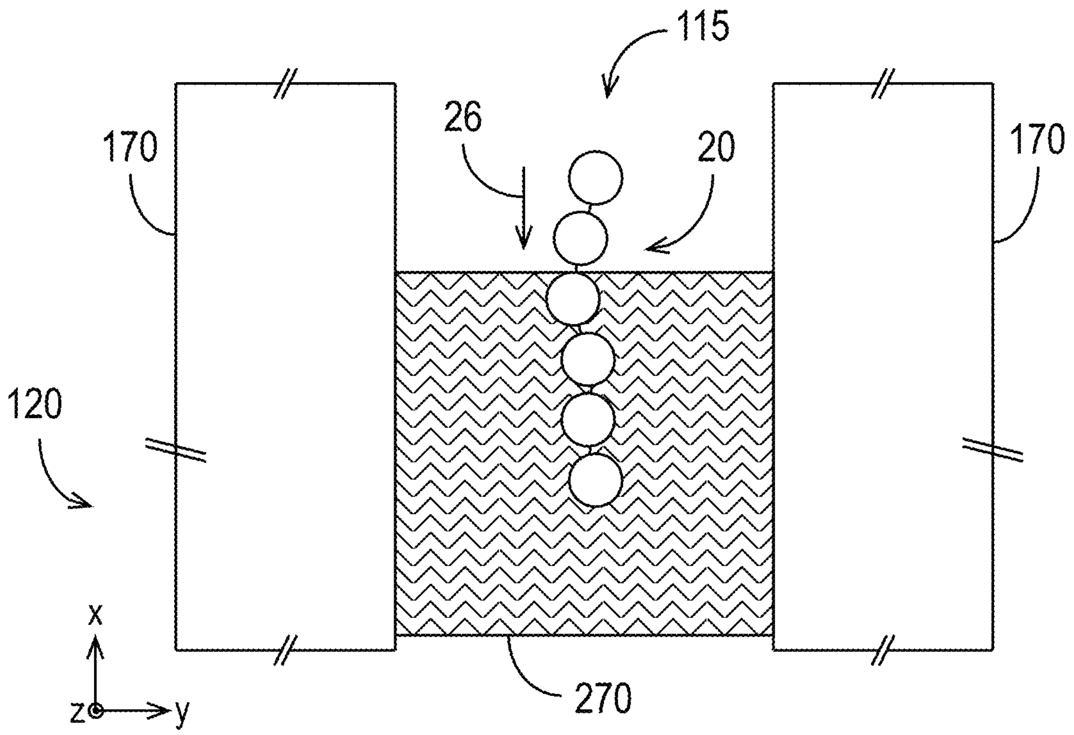
FIG. 5B is a diagram of a disintegrator that includes a waveguide situated so as to create evanescent waves to expose the contents of the fluidic channel to UVA radiation in accordance with some embodiments.

Another way the disintegrator 120 can create ROS in addition to divalent cations is by exposing the fluid in the fluidic channel 115 (e.g., a water bath) to UAV radiation of a suitable wavelength (e.g., 315-400 nm). The UAV radiation can be generated, for example, by evanescent waves from a waveguide. FIG. 5B is a diagram of a disintegrator 120 that includes a waveguide 270 situated so as to create evanescent waves to expose the contents of the fluidic channel 115 to UVA radiation. The waveguide 270 may be integrated into the substrate 170 such that it is situated below the fluidic channel 115 and is exposed to the contents of the fluidic channel 115.

Figure 5C:
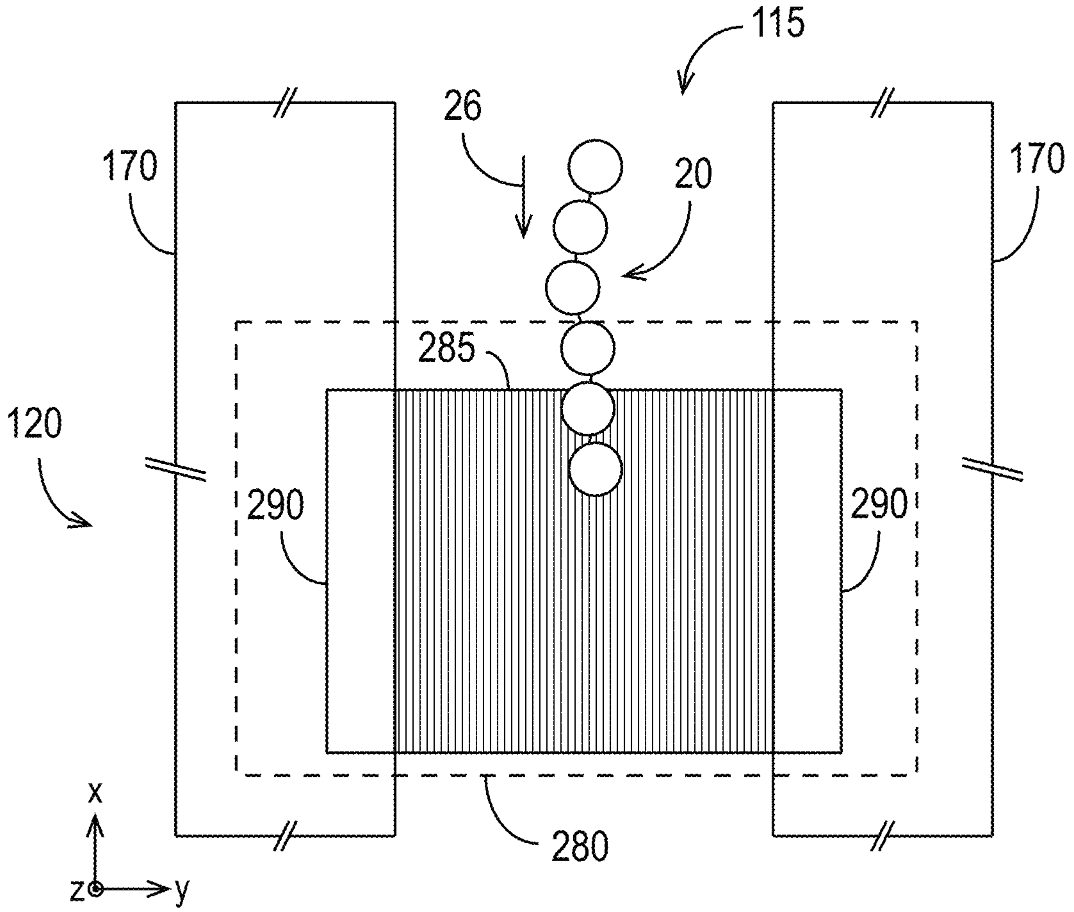
FIG. 5C shows an example of a disintegrator that includes a localized heater in accordance with some embodiments.

In some embodiments, the disintegrator 120 includes one or more components to accelerate disintegration and, therefore, increase throughput (sequencing speed). For example, the disintegrator 120 can include (or be coupled to) one or more components that allow the temperature of the contents of the fluidic channel 115 to be increased. As a specific example, increasing the temperature by 10 degrees Kelvin can at least double the rate of the reaction. FIG. 5C shows an example of a disintegrator 120 that includes a localized heater 280. The localized heater 280 includes a heater wire 285 coupled to a power source 290. The heater wire 285 can be situated on the floor of the fluidic channel 115. The heater wire 285 may be made of a high-resistance material (e.g., nichrome) and can convert electrical energy into heat energy through the process of resistive heating. The power source 290 applies an electric current through the heater wire 285, thereby heating the heater wire 285. The heat generated by the heater wire 285 is conducted from the heater wire 285 to the contents of the fluidic channel 115 through direct contact. Optionally, the localized heater 280 may include a thermostat or temperature controller to regulate the temperature. If included, the thermostat can monitor the temperature within the fluidic channel 115 and adjust the electrical current passing through the heater wire 285 to maintain a desired temperature. It is to be appreciated that, if included, the localized heater 280 does not have to heat a large region; instead, it can heat only a small region around the disintegrator 120.

Figure 5D:
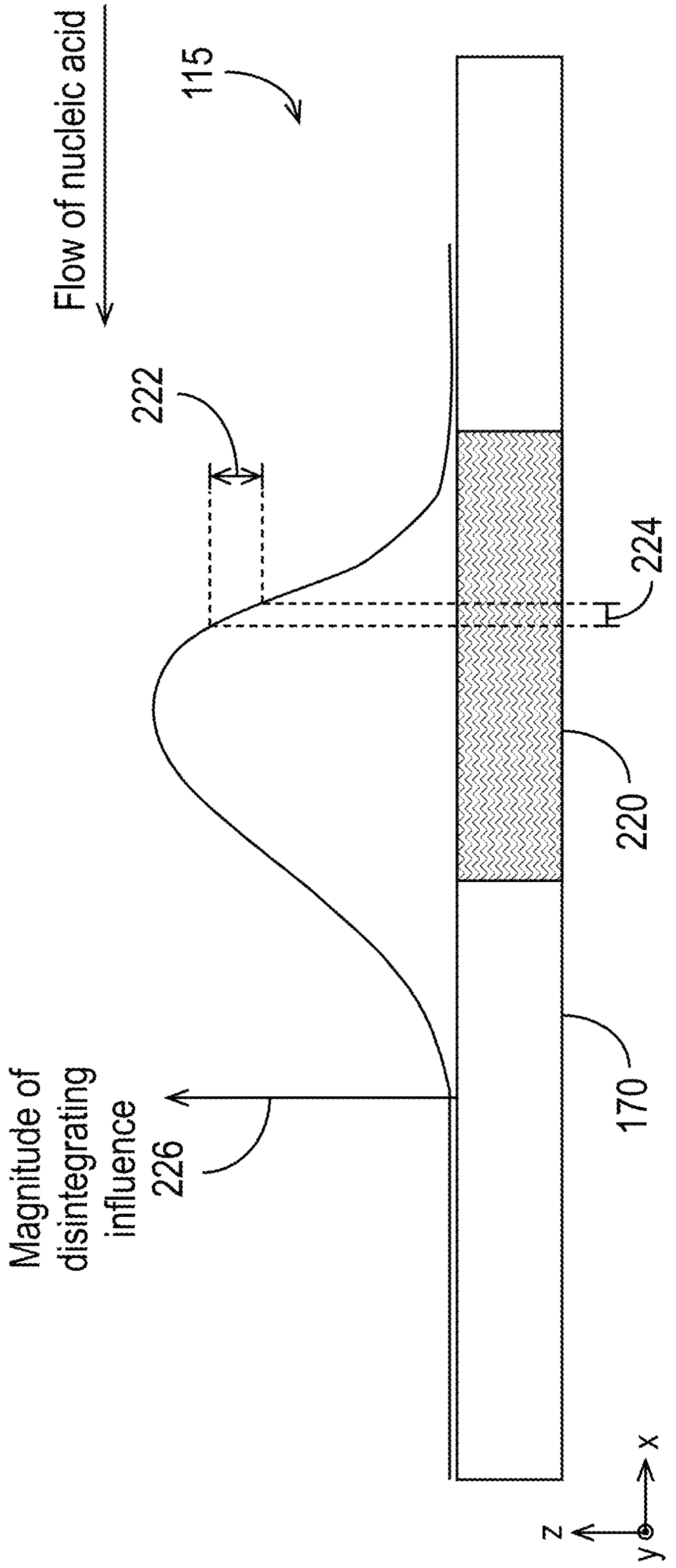
FIG. 5D is an illustration of the localization of disintegration in an example in accordance with some embodiments.

FIG. 5D is an illustration of the localization of disintegration in an example in which the system includes an assistive element 220 (e.g., a thin wire 250, a waveguide 270, etc.) situated below (and, depending on the nature of the assistive element 220, possibly exposed to the contents of) the fluidic channel 115 and configured to enhance operation of the disintegrator 120. As a nucleic acid flows (from right to left in the figure), it encounters a rapidly intensifying disintegration rate, represented by the curve. The spatial gradient of the disintegrator 120 influences how localized the disintegration is. A large spatial gradient results in precise disintegration. For example, as shown in FIG. 5D, the region of disintegration 224 is much smaller than the assistive element 220 (e.g., the thin wire 250, waveguide 270, etc.). The steeper the curve in the range of disintegration 222, the smaller the region of disintegration 224. Stated another way, assume disintegration occurs when the strength of the disintegrator 120 (shown in FIG. 5D as the magnitude of disintegrating influence 226) exceeds some magnitude (threshold) represented by the lower value of the range of disintegration 222. Assume also that the speed at which disintegration occurs depends on the amount by which the threshold is exceeded. Accordingly, a disintegrator 120 with a steep spatial gradient will expose the molecule 20 to a rapidly-intensifying effect over a short distance (e.g., along the x-axis in the coordinate system shown in FIG. 5D). In that case, the region of disintegration 224 (e.g., in the x-direction) will also be short. If the region of disintegration 224 is approximately the same as the length of a single nucleotide 25, then the molecule 20 (e.g., a DNA polymer) should disintegrate one nucleotide 25 at a time, as desired.

As is known, nucleotides have three parts: a sugar molecule (either deoxyribose in DNA or ribose in RNA), a phosphate group, and a nitrogenous base. Glycosidic bonds in nucleic acids are covalent bonds that connect the sugar molecules in the nucleotide monomers to the nitrogenous bases. The glycosidic bond in nucleic acids specifically refers to the bond between the sugar molecule and the nitrogenous base. This bond forms between the carbon atom at the 1' position of the sugar and the nitrogen atom of the base. In DNA, the nitrogenous bases are adenine (A), cytosine (C), guanine (G), and thymine (T), whereas in RNA, thymine is replaced by uracil (U). The sugar and phosphate are the same for all nucleotides, and therefore it is possible to improve the SNR further by removing this "constant bias" from the nucleotides by splitting the glycosidic bond between the amino acid and sugar. Accordingly, in some embodiments, in addition to cleaving single nucleotides 25, the disintegrator 120 also splits the glycosidic bond between the amino acid and sugar. The disintegrator 120 can use any suitable technique to split the glycosidic bond. For example, the disintegrator 120 can use enzymatic hydrolysis.

Figure 6:
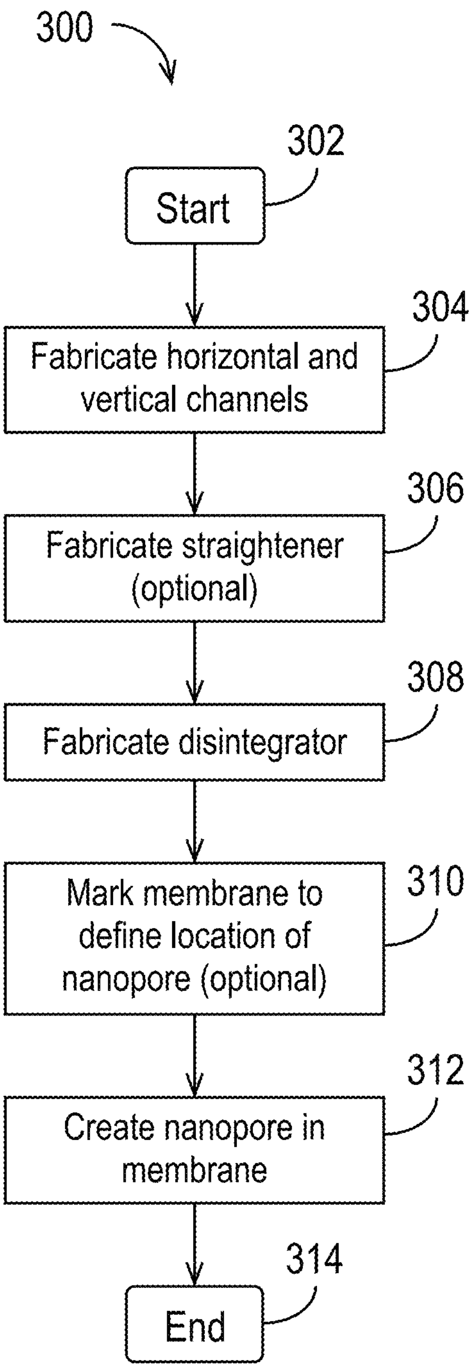
FIG. 6 is a flow diagram illustrating a method of making a system for single nucleotide sequencing in accordance with some embodiments.

FIG. 6 is a flow diagram illustrating a method 300 of making a device or system (e.g., any of the system 100, device 100A, device 100B, etc.) for single nucleotide sequencing. At block 302, the method 300 begins. At block 304, the fluidic channel 115 is fabricated in a substrate 170 (e.g., silicon). The fluidic channel 115 can be created in any suitable way, such as, for example, by using photolithography. As explained above, in some embodiments, the fluidic channel 115 has a horizontal portion 116 and a vertical portion 117. In such embodiments, the horizontal portion 116 and the vertical portion 117 are fabricated at block 304.

Optionally, at block 306, a straightener 110 is fabricated. It is to be appreciated that when the system includes the straightener 110, the block 306 can be performed at the same time as the block 304. In other words, the same manufacturing process (e.g., photolithography) used for the block 304 can also be used for the block 306 at the same time. For example, in embodiments in which the straightener 110 includes a quasi-2D structure (e.g., pillars 111), a single mask can define not only the fluidic channel 115, but also the quasi-2D structure of the straightener 110, and both the fluidic channel 115 and the quasi-2D structure can be fabricated during a single manufacturing step.

At block 308, the disintegrator 120 is fabricated using any suitable process (e.g., lithography). For example, the disintegrator 120 can be fabricated using an ion beam as described in D. Recht et al., "Supersaturating silicon with transition metals by ion implantation and pulsed laser melting," Journal of Applied Physics, 114(12), 2013, which is hereby incorporated by reference in its entirety for all purposes.

Optionally, at block 310, the membrane 180 can be marked to define the location of the nanopore 15 in the membrane 180. This may involve patterning the substrate 170 using lithographic techniques to define the position of the nanopore 15 in the membrane 180 on the back side 171 of the substrate 170.

At block 312, the nanopore 15 is created in the membrane 180 using any suitable technique. For example, the nanopore 15 can be created using dielectric breakdown. As will be appreciated, dielectric breakdown occurs when, under the influence of a strong electric field, a dielectric material experiences a sudden and significant increase in electrical conductivity, meaning that the dielectric material of the membrane 180, which was once insulating, starts to conduct electricity. Creating the nanopore 15 using dielectric breakdown involves introducing a tiny hole or pore (the nanopore 15) into the membrane 180, such as by applying a strong electric field to the membrane 180 (e.g., using the sensing electrode 18A and the sensing electrode 18B), which leads to dielectric breakdown and the formation of the nanopore 15. As dielectric breakdown occurs, the nanopore 15 is created at the location of the breakdown. The size and shape of the nanopore 15 depend on factors such as the properties of the membrane 180 and the applied voltage.

At block 314, the method 300 ends.

It is to be appreciated that other steps can be added to the method 300. For example, if included, the electrode 130A and the electrode 130B can be fabricated and/or added, such as by attaching the electrode 130A and/or the electrode 130B to the substrate 170. The electrode 130A and the electrode 130B can be added at any suitable time (e.g., after the block 306, after the block 312, etc.). As another example, the membrane 180 can be added to the back side 171 of the substrate 170 (e.g., before the block 304, before the block 310, etc.). As another example, the cover 160 can be placed on top of the substrate 170 (e.g., after the block 312). As noted above, the cover 160 may be removable.

The dimensions of the systems and devices (e.g., system 100, device 100A, device 100B) disclosed herein can be selected to reduce the likelihood that the disintegrator 120 cleaves off multi-nucleotide polymers (as opposed to single nucleotides) and to reduce the likelihood that cleaved single nucleotides pass each other in the fluidic channel 115. For illustrative purposes, the nucleic acid is assumed to be DNA in the derivations below. Those having ordinary skill in the art will be able to apply a similar approach for other types of molecules.

The speed of a DNA polymer through the disintegrator 120 is denoted by the variable S. The value of S is affected by the hydrostatic pressure. An increase (decrease) in hydrostatic pressure will result in an increase (decrease) in S. It is not necessarily the case that the motion of a DNA polymer through the fluidic channel 115 will be constant or consistent. It is assumed, however, that shorter DNA polymers generally travel faster through the fluidic channel 115 than longer DNA polymers.

As explained above, in some embodiments, the objective of the disintegrator 120 is to cleave single nucleotides from a molecule 20. The likelihood that the disintegrator 120 cleaves more than one nucleotide is likely affected by the value of S. In other words, for higher values of S, it is probably more likely that the disintegrator 120 will cleave a multi-nucleotide polymer. Accordingly, to reduce the occurrence or likelihood of multi-nucleotide polymers, the value of S should be decreased as needed by reducing hydrostatic pressure.

Figure 7:
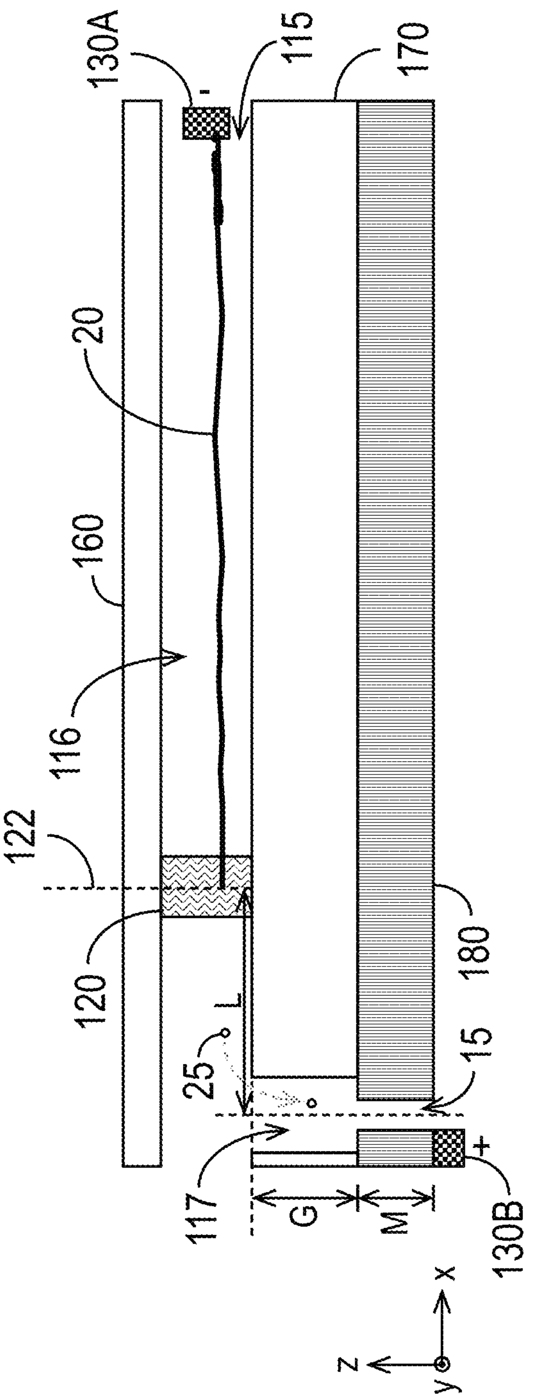
FIG. 7 illustrates various dimensions of a system in accordance with some embodiments.

Single nucleotides should not pass one another after disintegration as long as the nucleotides travel at a higher speed after disintegration than the molecule 20 travels in the fluidic channel 115. FIG. 7 illustrates various dimensions of a system 100 (e.g., a system using the device 100A, device 100B, etc.). The dimensions can be quantified as follows. Assume single nucleotides (e.g., nucleotide 25) travel through the fluidic channel 115 at a speed V, where V≥S, and through the nanopore 15 at a speed R. Define, $T_H$ as the time it takes for the DNA polymer moving at a speed S in the fluidic channel 115 to move a distance H equal to the pitch of one nucleotide 25 (e.g., ⅓ nm). Define $T_L$ as the time it takes for a single nucleotide 25 moving at a speed V to move a distance L from the location of disintegration 122 along the horizontal portion 116 of the fluidic channel 115 to the midpoint of the vertical portion 117 of the fluidic channel 115 (see FIG. 7). Define $T_{GM}$ as the time it takes for a single nucleotide 25 moving at a speed R to travel a distance of G+M, which is length of the vertical portion 117 plus the thickness of the membrane 180. (The vertical position of the nucleotide 25 in the horizontal portion 116 of the fluidic channel 115 is ignored in this analysis but could be included.) Using the defined notation, $$T_H = \frac{H}{S},\ T_L = \frac{L}{V},\ \text{and}\ T_{GM} = \frac{G+M}{R}.$$

If $$T_H > T_L > T_{GM}\left(\text{i.e., } \frac{H}{S} > \frac{L}{V} > \frac{G+M}{R}\right),$$

the nucleotide 25 accelerates through the horizontal portion 116, the vertical portion 117, and the nanopore 15. There are various ways to satisfy this constraint. To increase $T_H$, the hydrostatic pressure can be reduced to decrease the value of S. To modify $T_L$, the value of L can be modified (e.g., increased to increase $T_L$ and decreased to decrease $T_L$). The value of V is not considered to be an independent variable because both S and V are assumed to covary with the hydrostatic pressure. To decrease the value of $T_{GM}$, either the sum G+M can be decreased, or the value of R can be increased (e.g., by increasing the applied voltage on the electrode 130A and the electrode 130B). As explained above, the speed of the molecule 20 (and nucleotide 25) into/through the disintegrator 120 can be controlled by hydrostatic pressure and/or electrostatic potential (e.g., using the electrode 130A and the electrode 130B, if present).

As a specific example, assume that the length H of a single nucleotide is ⅓ nm, the speed S of DNA polymer in the fluidic channel 115 is 100 nucleotides per second (33.3. nm/s), the speed R of DNA through the nanopore 15 is 1 μs per nucleotide (333333.3 nm/s). To satisfy the constraint $T_{GM}<T_H$, the sum of the length of the vertical portion 117 and the membrane 180 thickness $$G+M < R\times\frac{H}{S} < 3333\ \text{nm}.$$

The speed V of a single nucleotide 25 in the fluidic channel 115 compared to the speed S of DNA polymer is what limits the length L of the disintegrator $$120\colon L < V\times\frac{H}{S}.$$

For example, if V=10×S, then L<3 nm. If V=100×S, then L<33 nm.

It is expected that decreasing the width of the horizontal portion 116 (using the coordinate system of FIG. 3A, in the y-direction) will decrease the mobility of DNA in the fluidic channel 115 and thus decrease the variability of disintegration. In other words, when the horizontal portion 116 is made narrower, it should reduce the occurrence of the disintegrator 120 cleaving multi-nucleotide polymers.

With respect to sampling, if it is assumed that the ionic current through the nanopore 15 is sampled at a rate of K samples per second, the number of samples N per nucleotide is $$N = K\times T_M = K\frac{M}{R},$$

where $T_M$ is the time for a nucleotide 25 to traverse the nanopore 15. The value of N needs to be greater than or equal to 1 for each nucleotide to be identifiable.

It should be appreciated that additional techniques can be included in the system (e.g., system 100, device 100A, device 100B) to help control the speed of the molecule 20 through the fluidic channel 115. Some techniques to control the speed of molecules are described in U.S. Patent Publication No. 2023/0176032, which published on Jun. 8, 2023 and is entitled "DEVICES, SYSTEMS, AND METHODS OF USING SMART FLUIDS TO CONTROL TRANSLOCATION SPEED THROUGH A NANOPORE" (corresponding to application Ser. No. 17/643,398, filed on Dec. 8, 2021), which is hereby incorporated by reference in its entirety for all purposes. Additional techniques to control the speeds of molecules are described in U.S. Patent Publication No. 2023/0176033, which published on Jun. 8, 2023 and is entitled "DEVICES, SYSTEMS, AND METHODS OF USING SMART FLUIDS TO CONTROL MOLECULE SPEEDS" (corresponding to application Ser. No. 17/643,401, filed on Dec. 8, 2021), which is hereby incorporated by reference in its entirety for all purposes. Still other techniques control the speeds of molecules are described in U.S. patent application Ser. No. 18/364,506, filed on Aug. 3, 2023 and entitled "Magnetic Control of Molecule Translocation Speed Through a Nanopore", which is hereby incorporated by reference in its entirety for all purposes.

Figure 8:
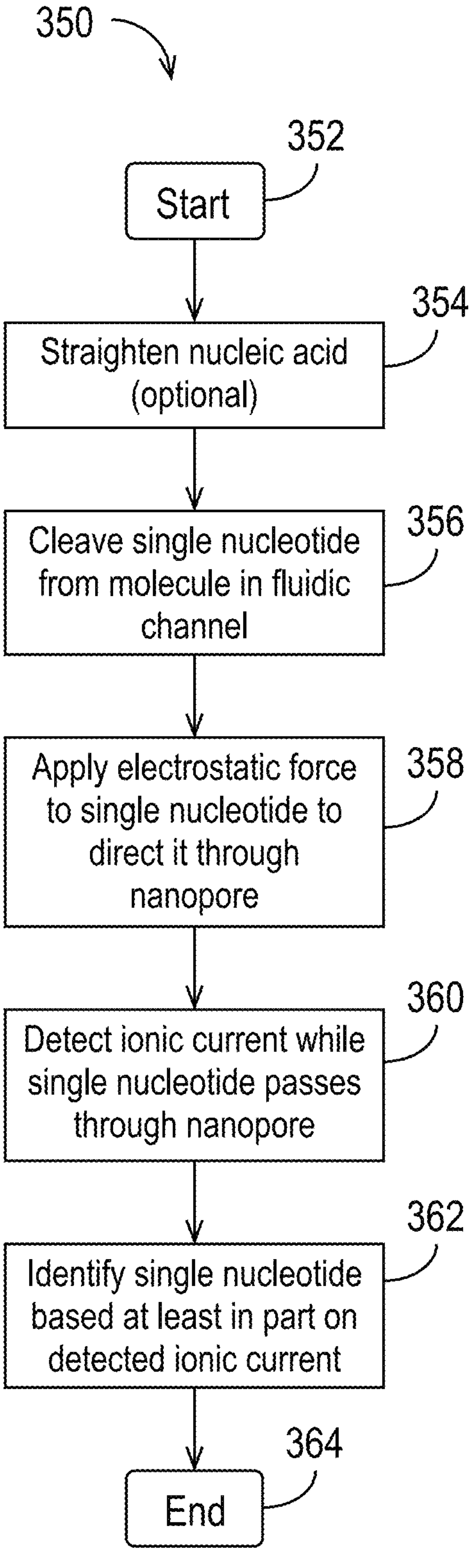
FIG. 8 is a flow diagram of a method of sequencing nucleic acids in accordance with some embodiments.

FIG. 8 is a flow diagram of a method 350 of sequencing nucleic acids in accordance with some embodiments. At block 352, the method 350 starts. At block 354, optionally, a molecule 20 in a fluidic channel 115 is straightened using any suitable technique (e.g., any of the techniques described above in the context of FIGS. 3A, 3B, 3C, 4A, 4B, and 4C).

At block 356, a portion of a molecule 20 (e.g., a single nucleotide 25) is cleaved from the molecule 20. The block 356 can be accomplished, for example, using a disintegrator 120, as described in detail above. The disintegrator 120 can, for example, cleave the portion of the molecule 20 (e.g., a single nucleotide 25) from the molecule 20 using a catalytic moiety with exonuclease-like activity (e.g., a divalent cation). As also explained above, in addition to cleaving single nucleotides 25, the disintegrator 120 can break the glycosidic bond between the amino acid and sugar. Alternatively, and as explained elsewhere, the disintegrator 120 can split a molecule 20 into small oligonucleotides, which could have different sizes (e.g., due to some bonds being easier to break than others). As another example, the disintegrator 120 can cleave off amino acids by breaking glycosidic bonds. As another example, the disintegrator 120 can cleave off nucleosides by breaking phosphoester bonds.

At block 358, an electrostatic force is applied (e.g., using an electrode pair 130) to divert the portion of the molecule 20 (e.g., the nucleotide 25) from the fluidic channel 115 and through a nanopore 15. Although block 358 is illustrated as following block 356 and block 354, it is to be appreciated that the electrostatic force can be applied while block 356 (and, if applicable, block 354) are being performed. As explained above, the applied electrostatic force should be larger than the hydrodynamic force that could otherwise result in the portion of the molecule 20 (e.g., the nucleotide 25) not being directed into the nanopore 15.

At block 360, the ionic current while the portion of the molecule 20 (e.g., the nucleotide 25) passes through the nanopore is detected. As explained above, in the case that the portion of the molecule 20 is a single nucleotide 25, depending on the thickness of the membrane 180, the rate at which the ionic current is sampled, and the speed V of the nucleotide 25 within the fluidic channel 115, multiple measurements (samples) may be taken for each nucleotide 25 that passes though the nanopore 15.

At block 362, the cleaved-off portion of the molecule 20 (e.g., the single nucleotide 25) is identified based at least in part on the detected ionic current. For example, if multiple samples are available, they can be averaged or otherwise combined. The identity of single nucleotides 25 or the composition of a cleaved-off portion of a molecule 20 can be determined in any suitable way. For example, the detected ionic current (raw or post-processed) can be compared to an expected ionic current for each possible nucleotide/portion to determine which of the possible nucleotides/portions matches best and is, therefore, presumed to be the nucleotide 25 or cleaved-off portion of the molecule 20.

At block 364, the method 350 ends.

Figure 9:
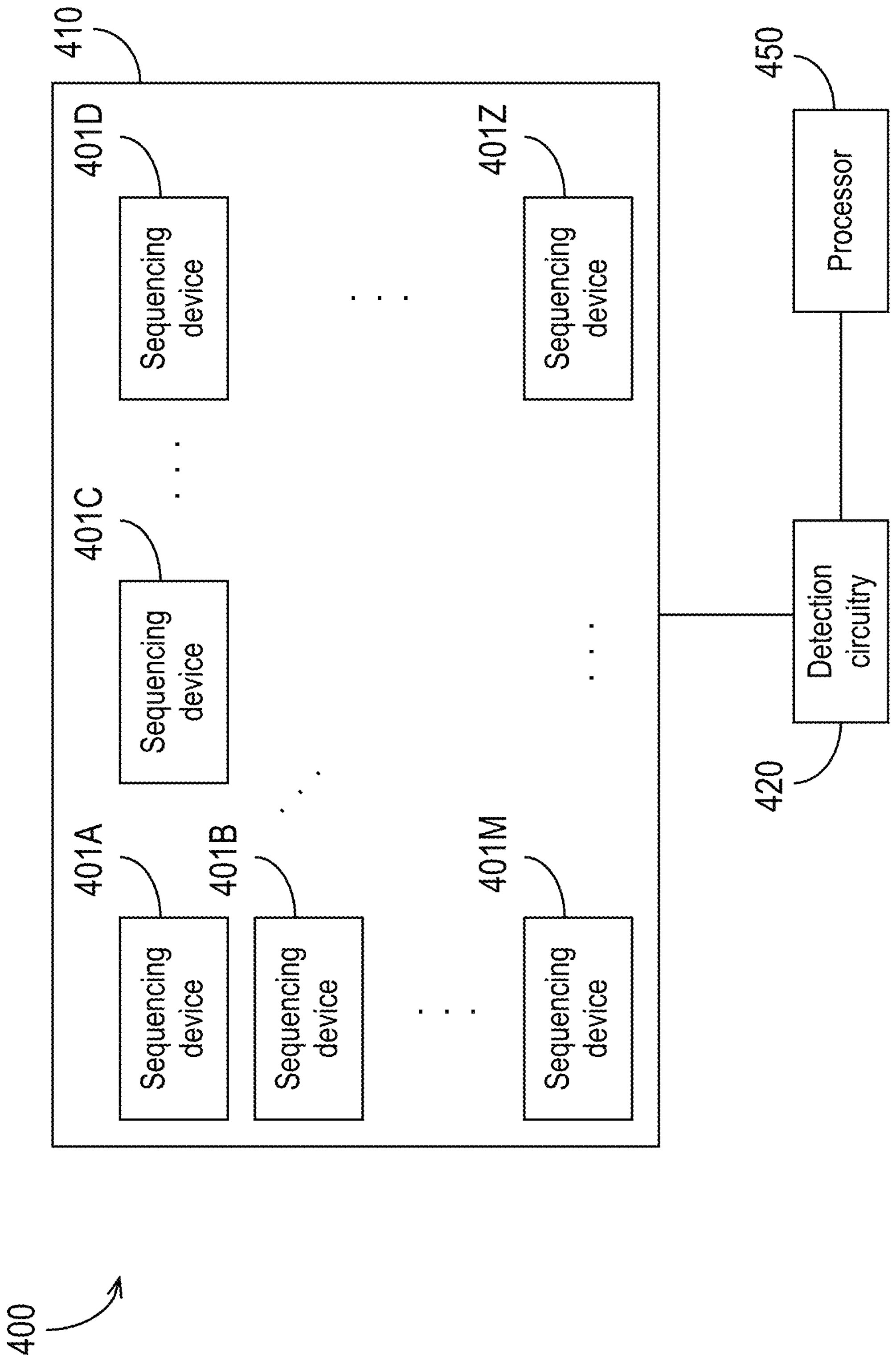
FIG. 9 is a diagram of a system that includes an array of sequencing devices in accordance with some embodiments.

The sequencing devices described herein (e.g., device 100A, device 100B, and variations thereof) can be incorporated into an array that can be included in a sequencing system. FIG. 9 is a diagram of an example of a system 400 that includes an array 410 of sequencing devices in accordance with some embodiments. As shown in FIG. 9, the array 410 includes a plurality of sequencing devices 401, namely the sequencing device 401A, the sequencing device 401B, the sequencing device 401C, the sequencing device 401D, the sequencing device 401M, and the sequencing device 401Z. The array 410 can be any device that applies the techniques described herein (e.g., device 100A, device 100B, etc.). The letters used in the reference numerals of FIG. 9 merely distinguish between instances of the sequencing devices 401. They are not intended to convey that the array 410 includes any particular number of sequencing devices 401.

The plurality of sequencing devices 401 may be arranged in the array 410 in any convenient manner. In the example system 400 shown in FIG. 9, the sequencing devices 401 of the array 410 are arranged in a grid of rows and columns.

The array 410 shown in FIG. 9 is coupled to detection circuitry 420, which is configured to detect ionic currents through the nanopores 15 of the sequencing devices 401. The detection circuitry 420 may include circuitry for controlling the array 410 and/or the plurality of sequencing devices 401, and/or for reading the ionic currents of the nanopores 15. For example, the detection circuitry 420 may include one or more voltage sources (e.g., for applying electrostatic forces to cause individual nucleotides 25 to pass through the nanopores 15, to apply voltage to the sensing electrodes 18, etc.), one or more amplifiers, and/or one or more analog-to-digital converters (or, more generally, digitizers). Some circuitry that can be included in the detection circuitry 420 is described in U.S. Patent Publication No. 2023/0258593, which published on Aug. 17, 2023 and is entitled "LOW NOISE AMPLIFIERS WITH FEEDBACK FOR NANOPORE APPLICATIONS" (for application Ser. No. 17/651,254, filed on Feb. 16, 2022), and U.S. Patent Publication No. 2023/0258592, which published on Aug. 17, 2023 and is entitled "LOW NOISE AMPLIFIERS WITH SHIELDS FOR NANOPORE APPLICATIONS" (for application Ser. No. 17/651,257, filed on Feb. 16, 2022), which are hereby incorporated by reference in their entireties for all purposes.

In the example system 400 shown in FIG. 9, the detection circuitry 420 is coupled to a processor 450. The processor 450 may be configured to gather ionic current measurements (e.g., raw data, which may be in digitized form) from the detection circuitry 420 and perform processing and/or sequencing tasks. For example, the processor 450 may be configured to determine identities of nucleotides passing through the nanopores 15 of the plurality of sequencing devices 401 based at least in part on the measured/detected ionic currents (or samples). As another example, the processor 450 may be configured to perform an assembly operation. As will be appreciated, assembly is the process of reconstructing a complete nucleic acid sequence (e.g., of a target organism or DNA fragment) from a collection of shorter sequences generated/detected during the sequencing process. For example, the processor 450 may be configured to generate a plurality of reads based on the ionic currents. The processor 450 may be configured to subject the reads to a quality-control process in which low-quality reads, sequencing errors, etc. are addressed (e.g., by trimming low-quality bases or adapters and filtering out sequences that do not meet certain quality criteria or that are known not to be correct/possible). The processor 450 may be configured to align or map the remaining reads to a reference genome, if one is available, or to assemble the reads into longer contiguous sequences. The processor 450 may be configured to analyze the overlapping regions of the reads to assemble them into contiguous sequences. This process may involve identifying regions of overlap between reads and merging them to create longer sequences. The processor 450 may be configured to perform multiple iterations of this process to generate longer and more accurate contiguous sequences. The processor 450 may be configured to order and orient the contiguous sequences relative to one another. The processor 450 may be configured to compare the assembled sequence to known sequences or perform additional operations and/or error checking to confirm specific regions. The processor 450 may be configured to analyze the final assembled nucleic acid sequence.

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to."

The terms "exemplary" and "embodiment" are used to express examples, not preferences or requirements.

The term "coupled" is used herein to express a direct connection/attachment as well as a connection/attachment through one or more intervening elements or structures.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature.

The term "substantially" is used to describe a structure, configuration, dimension, etc. that is largely or nearly as stated, but, due to manufacturing tolerances and the like, may in practice result in a situation in which the structure, configuration, dimension, etc. is not always or necessarily precisely as stated. For example, describing two lengths as "substantially equal" means that the two lengths are the same for all practical purposes, but they may not (and need not) be precisely equal at sufficiently small scales. As another example, a structure that is "substantially vertical" would be considered to be vertical for all practical purposes, even if it is not precisely at 90 degrees relative to horizontal.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

The invention claimed is:

1. A method of performing nucleic acid sequencing, the method comprising:

using a disintegrator situated in a fluidic channel of a sequencing device, cleaving off a portion of a nucleic acid molecule in the fluidic channel, wherein operation of the disintegrator is enhanced by an assistive element;

applying an electrostatic force to divert the portion of the nucleic acid molecule through a nanopore;

detecting an ionic current through the nanopore; and determining an identity of at least one nucleotide of the portion of the nucleic acid molecule based at least in part on the ionic current.

2. The method of claim 1, wherein cleaving off the portion of the nucleic acid molecule comprises inducing electrolysis.

3. The method of claim 1, wherein cleaving off the portion of the nucleic acid molecule comprises exposing a contents of the fluidic channel to UVA radiation.

4. The method of claim 1, further comprising controlling a speed of the nucleic acid molecule through the disintegrator.

5. A method of performing nucleic acid sequencing, the method comprising:

using a disintegrator situated in a fluidic channel of a sequencing device, cleaving off a portion of a nucleic acid molecule in the fluidic channel;

applying an electrostatic force to divert the portion of the nucleic acid molecule through a nanopore;

detecting an ionic current through the nanopore; and determining an identity of at least one nucleotide of the portion of the nucleic acid molecule based at least in part on the ionic current, wherein detecting the ionic current through the nanopore comprises sampling the ionic current a plurality of times while the portion of the nucleic acid molecule traverses the nanopore.

6. The method of claim 5, wherein the portion of the nucleic acid molecule is a single nucleotide, and the identity of the at least one nucleotide of the portion of the nucleic acid molecule is an identity of the single nucleotide.

7. The method of claim 5, wherein cleaving off the portion of the nucleic acid molecule comprises a catalytic moiety cleaving off the portion of the nucleic acid molecule.

8. The method of claim 7, wherein the catalytic moiety comprises a divalent cation.

9. The method of claim 5, wherein cleaving off the portion of the nucleic acid molecule comprises applying chemical hydrolysis.

10. The method of claim 5, further comprising straightening the nucleic acid molecule before cleaving off the portion of the nucleic acid molecule.

11. The method of claim 10, wherein straightening the nucleic acid molecule comprises directing the nucleic acid molecule through a structure situated in the fluidic channel.

12. The method of claim 5, further comprising controlling a speed of the nucleic acid molecule through the disintegrator.

13. The method of claim 12, wherein controlling the speed of the nucleic acid molecule through the disintegrator comprises applying a voltage through an electrode pair to control the speed of the nucleic acid molecule through the disintegrator.

14. The method of claim 12, wherein controlling the speed of the nucleic acid molecule through the disintegrator comprises applying hydrostatic pressure to control the speed of the nucleic acid molecule through the disintegrator.

15. A system for sequencing nucleic acids, the system comprising:

an array comprising a plurality of sequencing devices, each of the plurality of sequencing devices in the array comprising a respective fluidic channel, a respective disintegrator embedded in the respective fluidic channel, and a respective nanopore coupled to an exit end of the respective fluidic channel; and detection circuitry coupled to the array and configured to detect a plurality of nanopore currents, each of the plurality of nanopore currents corresponding to a respective sequencing device in the array, wherein each respective fluidic channel comprises a respective horizontal portion and a respective vertical portion.

16. The system recited in claim 15, wherein each of the plurality of sequencing devices in the array further comprises a respective straightener.

17. The system recited in claim 16, wherein the respective straightener comprises at least one of: (a) a progressive geometry, (b) a quasi-two-dimensional structure, (c) a three-dimensional structure, (d) a plurality of pillars, (e) a funnel, or (f) a plurality of spheres.

18. The system recited in claim 15, wherein each respective nanopore is situated at an exit end of the respective vertical portion of the respective fluidic channel.

19. The system recited in claim 15, wherein a thickness of each respective nanopore is larger than a pitch of a single nucleotide.

20. The system recited in claim 15, wherein each respective disintegrator comprises a catalytic moiety embedded in the respective fluidic channel.

21. The system recited in claim 20, wherein the catalytic moiety comprises a divalent cation.

22. The system recited in claim 15, wherein each respective disintegrator is configured to apply chemical hydrolysis.

23. The system recited in claim 15, wherein the array further comprises a wire, and further comprising a power source coupled to the wire and configured to induce electrolysis.

24. The system recited in claim 15, wherein each respective disintegrator comprises a respective waveguide configured to generate evanescent waves to expose a contents of the respective fluidic channel to UVA radiation.

25. The system recited in claim 15, wherein:

each respective horizontal portion includes a respective bottom surface defined by a top side of a substrate, and each respective nanopore is in a membrane situated on a back side of the substrate, the back side of the substrate being distal from the top side of the substrate.

* * * * *